(12) United States Patent
Suzuki et al.

(10) Patent No.: US 11,322,249 B2
(45) Date of Patent: May 3, 2022

(54) FEE-SETTING SYSTEM AND FEE-SETTING METHOD

(71) Applicant: OLYMPUS CORPORATION, Tokyo (JP)

(72) Inventors: Akira Suzuki, Tokyo (JP); Takeshi Nishiyama, Tokyo (JP); Akira Murata, Tokyo (JP); Takashi Nagata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 349 days.

(21) Appl. No.: 16/683,480

(22) Filed: Nov. 14, 2019

(65) Prior Publication Data
US 2020/0082936 A1     Mar. 12, 2020

Related U.S. Application Data

(63) Continuation of application No. PCT/JP2018/014922, filed on Apr. 9, 2018.

(30) Foreign Application Priority Data

May 15, 2017    (JP) .............................. JP2017-096618

(51) Int. Cl.
    *G16H 40/20*      (2018.01)
    *G16H 40/40*      (2018.01)
    *G06Q 30/06*      (2012.01)

(52) U.S. Cl.
    CPC ............. *G16H 40/20* (2018.01); *G06Q 30/06* (2013.01); *G16H 40/40* (2018.01)

(58) Field of Classification Search
    CPC ........ G16H 40/20; G16H 40/40; G16H 40/63; G06Q 30/06; G06Q 30/04; A61B 1/00
    See application file for complete search history.

(56) References Cited

U.S. PATENT DOCUMENTS

2005/0065405 A1*   3/2005   Hasegawa .............. A61B 1/123
                                                                         600/158

FOREIGN PATENT DOCUMENTS

JP      2001-160106 A     6/2001
JP      2002-345726 A    12/2002
(Continued)

OTHER PUBLICATIONS

Ofstead, Cori L., et al. "A glimpse at the true cost of reprocessing endoscopes." International Association of Healthcare Central Service Material Management (2017). (Year: 2017).*
(Continued)

*Primary Examiner* — Linh Giang Le
(74) *Attorney, Agent, or Firm* — Scully, Scott, Murphy & Presser, P.C.

(57) ABSTRACT

In a fee-setting system, an assessment unit assesses the degree of appropriateness in a medical facility regarding the use of a device relating to medical treatment used in the medical facility based on the degree of deviation and information regarding the medical facility, in which the degree of deviation that is obtained by comparing information indicating the usage status of the device that has been detected by a detection unit for detecting the usage status of the device with reference information regarding the method of using the device. A calculation unit calculates a fee to be charged to the medical facility based on the degree of appropriateness.

14 Claims, 30 Drawing Sheets

(56) References Cited

FOREIGN PATENT DOCUMENTS

| | | | |
|---|---|---|---|
| JP | 2006-218236 A | | 8/2006 |
| JP | 2006-230492 A | | 9/2006 |
| JP | 2006230492 A | * | 9/2006 |
| JP | 2006-276709 A | | 10/2006 |
| JP | 2009-066260 A | | 4/2009 |
| JP | 2009-072338 A | | 4/2009 |
| JP | 2011-014003 A | | 1/2011 |

OTHER PUBLICATIONS

International Preliminary Report on Patentability dated Nov. 19, 2019, together with the Written Opinion received in related International Application No. PCT/JP2018/014922.
International Search Report dated Jun. 26, 2018 issued in International Application No. PCT/JP2018/014922.

* cited by examiner

FIG.5

| EVALUATION ITEMS | EVALUATION REFERENCE | EXCELLENT | GOOD | FAIR | POOR |
|---|---|---|---|---|---|
| CONSUMABLE ITEM REPLACEMENT TIME LIMIT EXCEEDING ERROR | RATIO OF CONSUMABLE ITEMS THAT HAVE BEEN REPLACED WITHIN TIME LIMIT | 90% OR MORE | 90%~70% | 70%~50% | 50% OR LESS |
| NON-RECOMMENDED PRODUCT USE ERROR | RATIO OF RECOMMENDED PRODUCTS THAT ARE BEING USED | 90% OR MORE | 90%~70% | 70%~50% | 50% OR LESS |
| INSTALLATION ERROR | RATIO OF "NO ERROR" AND RATIO OF "ERROR THAT HAS BEEN FIXED BEFORE THE START OF CLEANING AFTER THE DETECTION OF THE ERROR" WITH RESPECT TO TOTAL NUMBER OF CLEANINGS | 90% OR MORE | 90%~70% | 70%~50% | 50% OR LESS |

| EVALUATION ITEMS | EVALUATION REFERENCE | EXCELLENT | GOOD | FAIR | POOR |
|---|---|---|---|---|---|
| USE COUNT OF CONSUMABLE ITEM | RATIO OF CONSUMABLE ITEMS THAT HAVE BEEN USED WITHIN STANDARD COUNT | 90% OR MORE | 90%~70% | 70%~50% | 50% OR LESS |
| NUMBER OF ELAPSED DAYS OF CONSUMABLE ITEM | RATIO OF CONSUMABLE ITEMS THAT HAVE BEEN USED WITHIN STANDARD NUMBER OF DAYS | 90% OR MORE | 90%~70% | 70%~50% | 50% OR LESS |
| EXPIRATION DATE OF CONSUMABLE ITEM | RATIO OF CONSUMABLE ITEMS THAT HAVE BEEN REPLACED WITHIN TIME LIMIT | 90% OR MORE | 90%~70% | 70%~50% | 50% OR LESS |
| MAINTENANCE DATE OF CLEANING MACHINE | RATIO OF CLEANING MACHINES THAT HAVE NOT EXCEEDED MAINTENANCE TIME LIMIT | 90% OR MORE | 90%~70% | 70%~50% | 50% OR LESS |
| NUMBER OF DAYS ELAPSED BEFORE CLEANING BY CLEANING MACHINE | RATIO OF CLEANING MACHINES THAT HAVE PERFORMED CLEANING WITHIN STANDARD NUMBER OF DAYS | 90% OR MORE | 90%~70% | 70%~50% | 50% OR LESS |
| CLEANING COUNT OF CLEANING MACHINE | TOTAL NUMBER OF CLEANINGS PERFORMED SINCE INTRODUCTION OF CLEANING MACHINE | 5000 TIMES OR LESS | 5000-10000 TIMES | 10000-20000 TIMES | 20000 TIMES OR MORE |

| EVALUATION ITEMS | EVALUATION REFERENCE | EXCELLENT | GOOD | FAIR | POOR |
|---|---|---|---|---|---|
| SCOPE WITH EXPIRED STORAGE TIME LIMIT | RATIO OF STORED SCOPES WITH EXPIRED STORAGE TIME LIMIT | 10% OR MORE | 10%~30% | 30%~50% | 50% OR MORE |
| TIME UNTIL CLEANING OF SCOPE AFTER EXAMINATION | RATIO OF SCOPES LEFT UNCLEANED FOR MORE THAN THE REFERENCE TIME | 10% OR MORE | 10%~30% | 30%~50% | 50% OR MORE |
| EXAMINATION IN WHICH SCOPE WITH EXPIRED STORAGE TIME LIMIT WAS USED | NUMBER OF EXAMINATIONS IN WHICH SCOPE WITH EXPIRED STORAGE TIME LIMIT WAS USED | 0 | — | — | ONE OR MORE TIMES |

| EVALUATION ITEMS | EVALUATION REFERENCE | EXCELLENT | GOOD | FAIR | POOR |
|---|---|---|---|---|---|
| SCOPES WHOSE STORAGE TIME LIMIT HAS PASSED SINCE THE LAST CLEANING | RATIO OF SCOPES THAT HAVE BEEN STORED WITHIN STORAGE TIME LIMIT | 90% OR MORE | 90%~70% | 70%~50% | 50% OR LESS |
| SCOPES THAT HAVE NOT BEEN CLEANED DESPITE HAVING BEEN USED FOR EXAMINATIONS UNTIL THE PREVIOUS DAY | RATIO OF SCOPES THAT HAVE BEEN CLEANED BY THE FOLLOWING DAY AFTER EXAMINATION | 90% OR MORE | 90%~70% | 70%~50% | 50% OR LESS |
| SCOPES USED FOR EXAMINATIONS EVEN THOUGH THE STORAGE TIME LIMIT HAS PASSED | THE NUMBER OF SCOPES USED FOR EXAMINATIONS EVEN THOUGH TIME LIMIT HAS PASSED | 0 | — | — | ONE OR MORE |
| SCOPES FOR WHICH WATER LEAKAGE INSPECTION HAS NOT BEEN PERFORMED | RATIO TO THE TOTAL NUMBER OF SCOPES FOR WHICH WATER LEAKAGE INSPECTION HAS BEEN PERFORMED AFTER THE EXAMINATION | 90% OR MORE | 90%~70% | 70%~50% | 50% OR LESS |
| SCOPES USED IN EXAMINATION EVEN AFTER DETECTION OF WATER LEAKAGE | THE NUMBER OF SCOPES USED IN AN EXAMINATION EVEN AFTER DETECTION OF WATER LEAKAGE | 0 | — | — | ONE OR MORE |

122

FEE-SETTING SYSTEM AND FEE-SETTING METHOD

CROSS-REFERENCE TO RELATED APPLICATIONS

This application is based upon and claims the benefit of priority from the prior Japanese Patent Applications No. 2017-096618, filed on May 15, 2017, and International Application No. PCT/JP2018/014922, filed on Apr. 9, 2018, the entire contents of which are incorporated herein by reference.

BACKGROUND OF THE INVENTION

1. Field of the Invention

The present invention relates to a fee-setting system and a fee-setting method for setting a maintenance fee for a medical device.

2. Description of the Related Art

Many medical devices such as endoscopic examination devices are used in medical facilities. Devices for inspecting and/or maintaining medical devices are also used. For example, in an endoscopy department, a cleaning machine for cleaning endoscopes is used. Hereinafter, in this specification, the term "medical device" is used to mean a medical device in a broad sense. A medical device in a broad sense is a concept including a device used in a medical field in order to inspect or maintain a medical device in a narrow sense that directly performs a medical action on a patient.

Many medical devices require maintenance, and medical facilities where medical devices are installed usually have a medical device maintenance contract with a medical device sales/leasing company or an independent maintenance management company. Hereinafter, medical device sales companies, medical device leasing companies, and independent maintenance management companies are collectively referred to as maintenance service providers. In the case of a failure in a medical device in a medical facility, contact is made with the maintenance service provider so as to request a service person to repair the medical device.

Currently, regarding medical device maintenance contracts, a flat fee structure is applied to both medical facilities where the method of using medical devices is good such that service persons are rarely called and medical facilities where the method of using medical devices is poor such that service persons are frequently called. In terms of a fee structure, there is currently no incentive to improve the method of using medical devices.

SUMMARY OF THE INVENTION

In this background, a purpose of the present invention is to provide a technology for improving an incentive to appropriately use medical devices.

A fee-setting system according to one embodiment of the present invention includes: an assessment unit configured to assess the degree of appropriateness in a medical facility regarding the use of a device relating to medical treatment used in the medical facility based on the degree of deviation and information regarding the medical facility, in which the degree of deviation that is obtained by comparing information indicating the usage status of the device that has been detected by a detection unit for detecting the usage status of the device with reference information regarding the method of using the device; and a calculation unit configured to calculate a fee to be charged to the medical facility based on the degree of appropriateness.

Another embodiment of the present invention relates to a fee-setting method. This method includes: the assessment unit assessing the degree of appropriateness in a medical facility regarding the use of a device relating to medical treatment used in the medical facility based on the degree of deviation and information regarding the medical facility, in which the degree of deviation that is obtained by comparing information indicating the usage status of the device that has been detected by a detection unit for detecting the usage status of the device with reference information regarding the method of using the device; and the calculation unit calculating a fee to be charged to the medical facility based on the degree of appropriateness.

Yet another embodiment of the present invention relates to a processing device. This device includes an assessment unit configured to assess the degree of appropriateness in a medical facility regarding the use of a device relating to medical treatment used in the medical facility based on the degree of deviation and information regarding the medical facility, in which the degree of deviation that is obtained by comparing information indicating the usage status of the device that has been detected by a detection unit for detecting the usage status of the device with reference information regarding the method of using the device, and output the degree of appropriateness and the information regarding the medical facility in order to calculate a fee to be charged to the medical facility.

Still another embodiment of the present invention relates to a medical device. This medical device is a medical device installed in a medical facility, including: a detection unit configured to detect the usage status of the medical device; an assessment unit configured to assess the degree of appropriateness regarding the use of the device in the medical facility based on the degree of deviation obtained by comparing information indicating the usage status with reference information regarding the method of using the device: and an transmission unit configured to transmit the degree of appropriateness and the information regarding the medical facility to a device that calculates a fee to be charged to the medical facility via a communication network.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 5 is a diagram showing an example of an evaluation table according to the second embodiment;

FIG. 8 is a diagram showing an example of an evaluation table according to the third embodiment;

FIG. 11 is a diagram showing an example of an evaluation table according to the fourth embodiment;

FIG. 16 is a diagram showing an example of an evaluation table according to the fifth embodiment;

DETAILED DESCRIPTION OF THE INVENTION

The invention will now be described by reference to the preferred embodiments. This does not intend to limit the scope of the present invention, but to exemplify the invention.

First Embodiment

Figure 1:
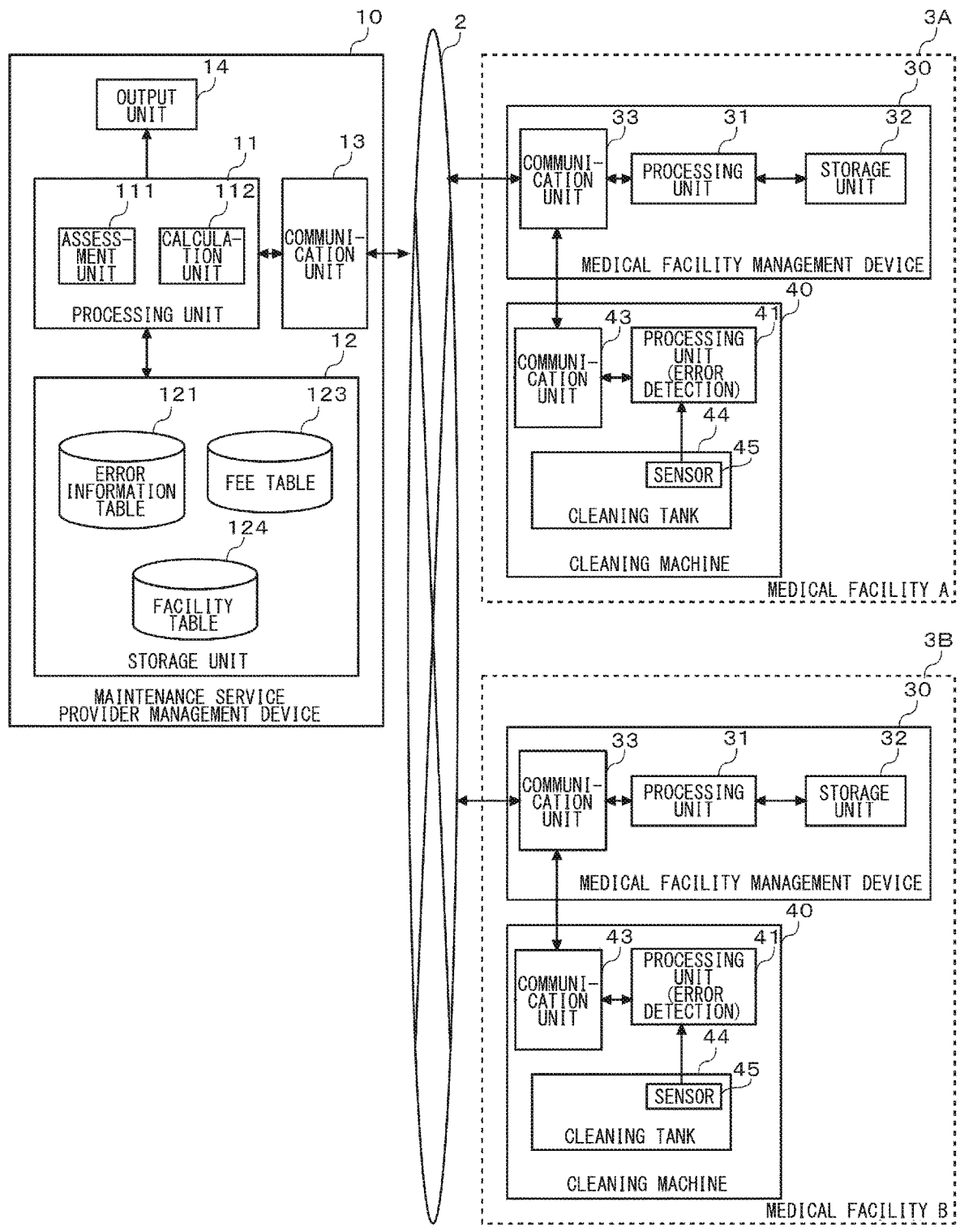
FIG. 1 is a block diagram showing the configuration of a fee-setting system according to the first embodiment of the present invention.

FIG. 1 is a block diagram showing the configuration of a fee-setting system according to the first embodiment of the present invention. A maintenance service provider management device 10 is a device constructed in a system department of a maintenance service provider and is constructed by at least one server or PC and peripheral devices such as a printer.

The maintenance service provider has a maintenance contract with multiple medical facilities for a medical device sold or leased by the maintenance service provider. In FIG. 1, the maintenance service provider has a maintenance contract with two medical facilities, a medical facility A (3A) and a medical facility B (3B). In the first embodiment, a medical facility management device 30 and a cleaning machine 40 are installed in each of the medical facility A (3A) and the medical facility B (3B).

The maintenance service provider management device 10 and the medical facility management devices 30 of the medical facility A (3A) and the medical facility B (3B) are connected via an external network 2. For the external network 2, the Internet or a dedicated line can be used.

The medical facility management device 30 according to the first embodiment is a device that is installed in an endoscopy department and constructs a system for supporting endoscopic work. The medical facility management device 30 is constructed by at least one server or PC and a peripheral device. The medical facility management device 30 is connected to the cleaning machine 40 via an internal network such as a hospital LAN. The medical facility management device 30 can be linked with another system in the medical facility. For example, it can be linked with an ordering system, an electronic medical record system, and a medical accounting system.

The medical facility management device 30 includes a processing unit 31, a storage unit 32, and a communication unit 33. The processing unit 31 can be realized by the cooperation of hardware resources and software resources or only by hardware resources. As the hardware resources, processors, ROM, RAM, and other LSIs can be used. A CPU, a GPU, and the like can be used as the processors. Programs such as operating systems and applications can be used as the software resources. The storage unit 32 includes a non-volatile recording medium such as HDD, SSD, etc. The communication unit 33 executes a communication process that complies with a predetermined communication protocol. For example, the communication unit 33 executes a communication process with the maintenance service provider management device 10 that complies with TCP/IP and executes a communication process that complies with the cleaning machine 40 and Ethernet (registered trademark). In communication via the external network 2, a secure sockets layer (SSL) communication is preferably used.

The cleaning machine 40 is a device for cleaning and disinfecting a scope and scope accessories used in an endoscopy examination. The cleaning machine 40 includes a processing unit 41, a communication unit 43, a cleaning tank 44, and a sensor 45. At least one scope is installed in the cleaning tank 44. The sensor 45 is a flow sensor for detecting the flow rate of water or cleaning liquid or a pressure sensor for detecting the pressure of water or cleaning liquid installed in a flow channel in the cleaning tank 44.

The processing unit 41 can be realized by the cooperation of hardware resources and software resources or only by hardware resources. As the hardware resources, processors, ROM, RAM, and other LSIs can be used. As the processors, microcomputers, DSPs, FPGAs, and the like can be used. As the software resources, firmware and other programs can be used. The communication unit 43 executes a communication process that complies with a predetermined communication protocol. For example, the communication unit 43 executes a communication process with the medical facility management device 30 that complies with Ethernet (registered trademark).

The maintenance service provider management device 10 includes a processing unit 11, a storage unit 12, a communication unit 13, and an output unit 14. The processing unit 11 includes an assessment unit 111 and a calculation unit 112. The storage unit 12 includes an error information table 121, a fee table 123, and a facility table 124.

The processing unit 11 can be realized by the cooperation of hardware resources and software resources or only by hardware resources. As the hardware resources, processors, ROM, RAM, and other LSIs can be used. A CPU, a GPU, and the like can be used as the processors. Programs such as operating systems and applications can be used as the software resources. The storage unit 12 includes a non-volatile recording medium such as HDD, SSD, etc. The communication unit 13 executes a communication process that complies with a predetermined communication protocol. For example, the communication unit 13 executes communication processes with the respective medical facility management devices 30 of the medical facility A (3A) and the medical facility B (3B) that complies with TCP/IP. The output unit 14 includes a display and/or a printer.

Figure 2:
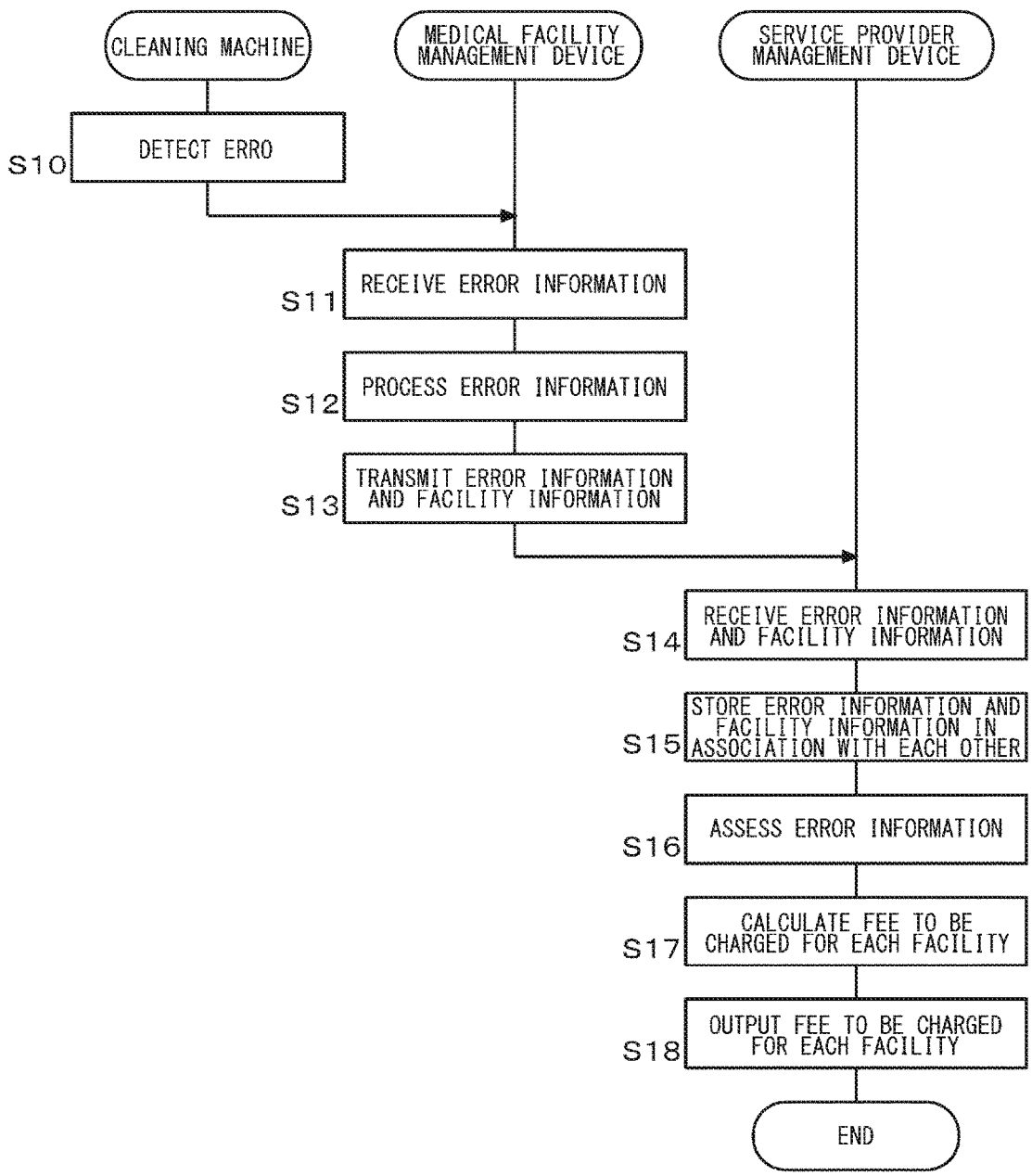
FIG. 2 is a flow chart showing the flow of a fee-setting process according to the first embodiment.

FIG. 2 is a flow chart showing the flow of a fee-setting process according to the first embodiment. The processing unit 41 of the cleaning machine 40 detects the usage status of the cleaning machine 40. In the first embodiment, the processing unit 41 detects whether the cleaning machine 40 is properly used or an error has occurred (S10). If the user incorrectly operates the cleaning machine 40, an error occurs. More specifically, the user connects a tube of each kind of scope to a predetermined position of the cleaning tank 44 and presses a pre-check switch (not shown) of the cleaning machine 40 so as to flush water into the pipeline of the scope before the cleaning is started. The processing unit 41 acquires a detection value from the sensor 45 installed in the flow channel. The processing unit 41 compares the detection value that has been acquired with a preset detection value (reference value) obtained in a state in which the tube is normally connected and calculates the difference between the two. If the difference is larger than a threshold value, the processing unit 41 determines that the tube is incorrectly connected and detects an error.

When it is determined that the connection is incorrect, the processing unit 41 can display a message indicating that the connection is incorrect on a display screen of the cleaning machine 40. Instead of displaying a message, the processing unit 41 may give notification using a sound indicating that the connection is incorrect.

The processing unit 41 passes error information including error detection to the communication unit 43, and the communication unit 43 transmits the error information to the medical facility management device 30 via the internal network. The error information is information reflecting the usage status of the cleaning machine 40.

The communication unit 33 of the medical facility management device 30 receives error information from the cleaning machine 40 and passes the error information to the processing unit 31 (S11). The processing unit 31 processes the received error information (S12). More specifically, the processing unit 31 performs the storage of the error information, the processing of the error information, the selection of error information to be transmitted, and the like. The processing of the error information is a process of classifying the error information (raw data) that has been acquired into parameters such as error type, error frequency, and recurrence rate.

The processing unit 31 adds facility information regarding the medical facility to the processed error information and passes the processed error information to the communication unit 33. The facility information includes at least identification information of the medical facility. The communication unit 33 transmits the error information and the facility information to the maintenance service provider management device 10 via the external network 2 (S13).

The communication unit 13 of the maintenance service provider management device 10 receives the error information and the facility information via the external network 2 and passes the error information and the facility information to the processing unit 11 (S14). The processing unit 11 stores the error information and the facility information that have been received, in association with each other in the error information table 121 (S15).

At a predetermined timing, the assessment unit 111 reads the error information and the facility information stored in the error information table 121 and assesses the error information (S16). More specifically, the assessment unit 111 compares the error information related to the user's incorrect operation as information indicating the usage status of the cleaning machine 40 with reference information regarding the operation method as information regarding the method of using the cleaning machine 40 so as to assess whether or not the cleaning machine 40 has been appropriately used. For example, the assessment unit 111 classifies cleaning in which an error has occurred into a cleaning in which pre-check has been performed again to fix incorrect connection and a cleaning in which cleaning has been performed while having the incorrect connection and sums up the cleanings. The assessment unit 111 then compares the cleanings as classified and summed up with the reference information. The timing for performing the assessment is set, for example, at a predetermined time on the closing date of the month.

By comparing the detection value of the flow rate and/or pressure of the cleaning liquid detected by the sensor 45 with the reference value of the flow rate and/or pressure of the cleaning liquid, the assessment unit 111 assesses whether a scope has been appropriately set in the cleaning machine 40. When making this assessment, the processing unit 41 of the cleaning machine 40 includes the detection value of the flow rate and/or pressure of the cleaning liquid in the error information.

The calculation unit 112 reads fee information corresponding to various errors that occur when using the cleaning machine 40 from the fee table 123. The calculation unit 112 calculates a fee to be charged (for example, a maintenance fee) for each medical facility based on the fee information that has been read, the assessment result by the assessment unit 111, and the facility information (S17). For example, the calculation unit 112 discounts, from the basic fee, the fee corresponding to the number of cleanings (cleaning count) in which incorrect connection of a tube has not been detected or the number of cleanings in which incorrect connection has been fixed through connecting a tube again after the incorrect connection has been detected, and calculate a final fee to be charged. At that time, the calculation unit 112 may weigh the fee to be charged according to the type of error and/or the frequency of occurrence. The calculation unit 112 stores the calculated fee to be charged and the facility information in the facility table 124 in association with each other.

Caused by a user's operation, the output unit 14 outputs the fee to be charged and the facility information stored in the facility table 124 (S18). For example, the output unit 14 causes the fee to be charged and the facility information to be displayed on a display or printed out. At that time, the fee to be charged and the facility information may be printed out in the form of an invoice to the facility. An electronic file (for example, a PDF file) in the form of an invoice may be generated.

As described above, according to the first embodiment, a fee to be charged for each facility can be calculated based on the error information acquired from the cleaning machine 40. Therefore, a facility where the cleaning machine 40 is appropriately used can reduce the maintenance cost of the cleaning machine 40. Thereby, education and enlightenment for appropriately using the cleaning machine 40 can be expected, and a reduction in the time for a medical practitioner to deal with the error of the cleaning machine 40, that is, the time spent for work other than the regular work can be therefore expected.

Hereinafter, an exemplary variation of the first embodiment will be described. In the step S17 of FIG. 2, the calculation unit 112 calculates a fee to be charged for each facility based on the assessment result in the assessment unit 111, the facility information, the fee information corresponding to various errors, the number of license holders who belong to the facility, and fee information corresponding to the qualification level of the qualified persons (S17). For example, the calculation unit 112 calculates a final fee to be charged by discounting from the basic fee a fee that corresponds to an error that has not occurred and a fee that corresponds to the number of qualified staff and/or their qualification level.

For example, the total number of clinical engineers and certified specialists for endoscopic work is used for the number of the qualified staff. The discount rate increases as the number of qualified staff increases and as the qualification level increases. Qualified staff information indicating the number and qualification level of qualified staff of each medical facility may be collectively managed by providing a qualified staff table (not shown) in the storage unit 12 of the maintenance service provider management device 10 or may be included in the facility information transmitted from the medical facility management device 30 of the medical facility to the maintenance service provider management device 10.

As described above, according to the exemplary variation of the first embodiment, the same effects as those of the first embodiment can be obtained, and the fee to be charged for each facility can be further finely optimized in accordance with the qualified staff information for each facility.

Second Embodiment

Figure 3:
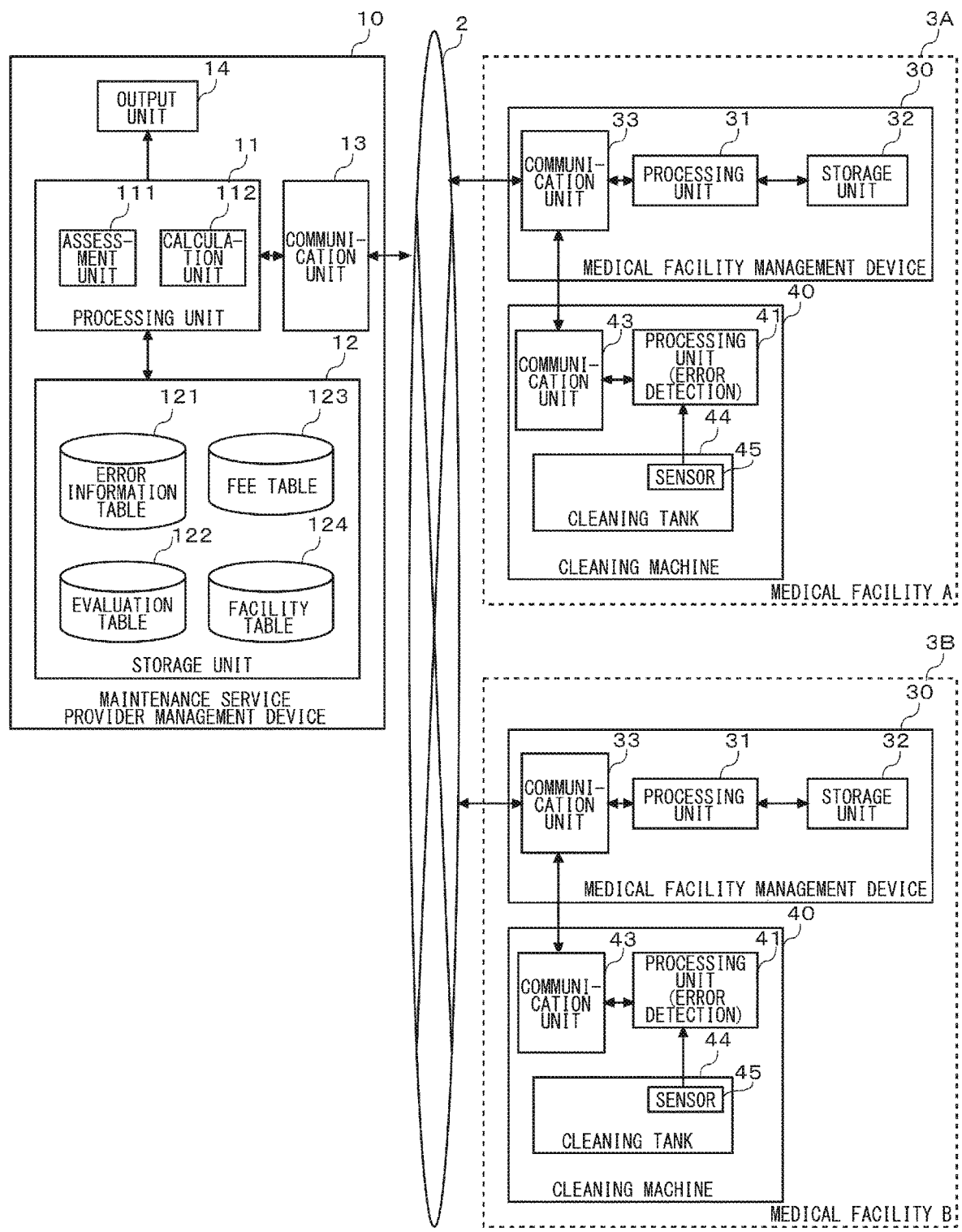
FIG. 3 is a block diagram showing the configuration of a fee-setting system according to the second embodiment of the present invention.

FIG. 3 is a block diagram showing the configuration of a fee-setting system 1 according to the second embodiment of the present invention. The storage unit 12 of the maintenance service provider management device 10 according to the second embodiment includes an evaluation table 122 in addition to an error information table 121, a fee table 123, and a facility table 124. Other components are the same as those of the fee-setting system 1 according to the first embodiment.

Figure 4:
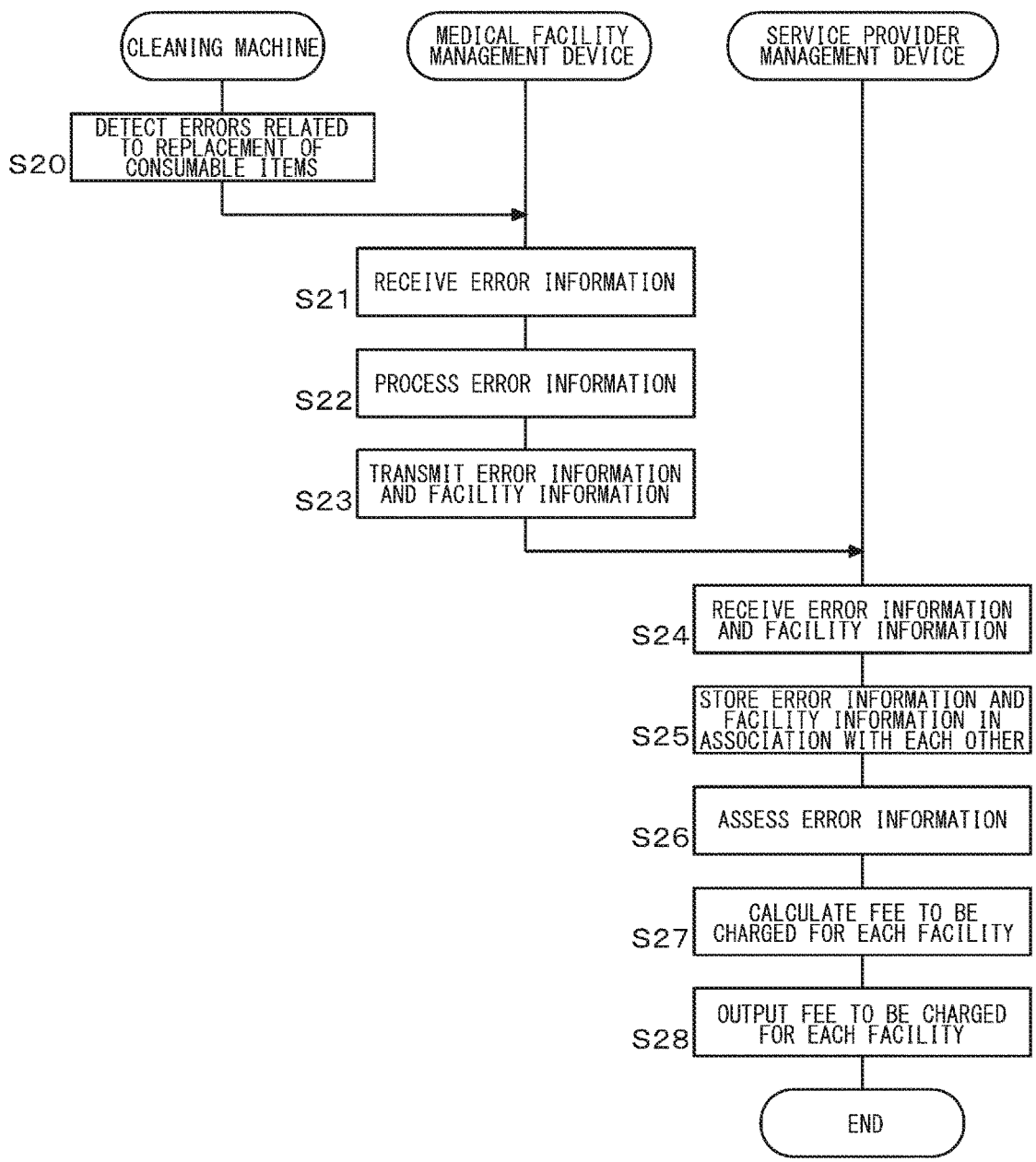
FIG. 4 is a flow chart showing the flow of a fee-setting process according to the second embodiment.

FIG. 4 is a flow chart showing the flow of a fee-setting process according to the second embodiment. The processing unit 41 of the cleaning machine 40 detects the usage status of the cleaning machine 40. In the second embodiment, the processing unit 41 detects errors related to the replacement of consumable items of the cleaning machine 40 (S20). More specifically, the processing unit 41 detects errors such as (1) an exceeding error for exceeding the replacement time limit for the consumable items, the maximum number of use, or the maximum number of days of use, (2) a non-recommended product error for the replacement with consumable items other than recommended products, and (3) an installation error for not properly installed consumable items. The consumable items of the cleaning machine 40 include a disinfectant solution, a cleaning solution, a filter, and the like.

The (1) exceeding error can be detected from log information on the date of installation of a consumable item managed in the processing unit 41 of the cleaning machine 40 and/or log information on the number of times the consumable item has been used. That is, if the number of days elapsed from the most recent installation date of the consumable item exceeds a threshold value, or if the number of times or the number of days the consumable item has been used exceeds a threshold value, an exceeding error for the consumable item occurs. The (2) non-recommended product error is detected by reading the model number information with a reader (not shown) of the cleaning machine 40 from a tag such as a radio frequency identifier (RFID) attached to the consumable item. If the model number is different from the model number of a recommended product (regular product) or if the model number information cannot be read, the processing unit 41 determines that the consumable item is a non-recommended product. Regarding the (3) installation error, whether or not the consumable item has been correctly installed is detected by a sensor (not shown) installed at the installation position of the consumable item.

The processing unit 41 passes error information including error detection to the communication unit 43, and the communication unit 43 transmits the error information to the medical facility management device 30 via the internal network. The communication unit 33 of the medical facility management device 30 receives the error information from the cleaning machine 40 and passes the error information to the processing unit 31 (S21). The processing unit 31 processes the received error information (S22). The processing unit 31 adds facility information regarding the medical facility to the processed error information and passes the processed error information to the communication unit 33. The communication unit 33 transmits the error information and the facility information to the maintenance service provider management device 10 via the external network 2 (S23).

The communication unit 13 of the maintenance service provider management device 10 receives the error information and the facility information via the external network 2 and passes the error information and the facility information to the processing unit 11 (S24). The processing unit 11 stores the error information and the facility information that have been received, in association with each other in the error information table 121 (S25).

At a predetermined timing, the assessment unit 111 reads the error information and the facility information stored in the error information table 121 and assesses the error information (S26). For example, the assessment unit 111 can assess whether or not the consumable item has been replaced at an appropriate time by comparing the replacement date of the consumable item with the expiration date of the consumable item. Further, the assessment unit 111 can assess whether or not the consumable item has been replaced at an appropriate time by comparing the acquired value of the number of times the consumable item has been used (use count) with a reference value of the use count of the consumable item. The assessment unit 111 can assess whether or not the consumable item has been replaced at an appropriate time by comparing the acquired value of the number of days of use of the consumable item with a reference value of the number of days of use of the consumable item. Further, the assessment unit 111 can assess whether or not the consumable item has been replaced with an appropriate product by comparing the model number of the consumable item that has been detected with the model number of the regular product.

The assessment unit 111 can read evaluation reference information in the evaluation table 122, compare the error information and the evaluation reference information, and rank the degree of appropriateness regarding the use of the cleaning machine 40 based on the degree of deviation between the two.

FIG. 5 is a diagram showing an example of an evaluation table 122 according to the second embodiment. Evaluation items shown in FIG. 5 are a consumable item replacement time limit exceeding error, a non-recommended product use error, and an installation error. The evaluation on the consumable item replacement time limit exceeding error is determined based on the ratio of consumable items that have been replaced within the time limit to all the consumable items. "Excellent" is given when the ratio is 90% or more, "Good" is given when the ratio is between 90% and 70%, "Fair" is given when the ratio is between 70% and 50%, and "Poor" is given when the ratio is 50% or less.

The evaluation on the non-recommended product use error is determined based on the ratio of recommended products that are being used to all the consumable items. The ranking method for the ratio is the same as that for the consumable item replacement time limit error. The evaluation on the installation error is determined based on the ratio of "no error" and the ratio of "error that has been fixed before the start of cleaning after the detection of the error" with respect to the total number of cleanings. The ranking method for the ratio is the same as that for the consumable item replacement time limit error.

FIG. 4 is referred back. The calculation unit 112 reads fee information corresponding to various errors that occur when replacing a consumable item of the cleaning machine 40 from the fee table 123. The calculation unit 112 calculates a fee to be charged (for example, a maintenance fee) for each cleaning machine 40 based on the fee information that has been read, the assessment result by the assessment unit 111, and the facility information (S27). For example, the calculation unit 112 discounts, from the basic fee, the fee corresponding to the ratio of consumable items that have been replaced within the time limit, the ratio of recommended products that are being used, and the number of cleanings performed without the occurrence of an error, and calculate a final fee to be charged. At this time, the fee to be charged may be calculated in comparison with the degree of appropriateness regarding the use of the cleaning machine 40 ranked by the assessment unit 111. If a plurality of cleaning machines 40 are installed in one facility, a fee to be charged for each facility is calculated based on a fee system corresponding to the number of cleaning machines 40. The calculation unit 112 may weigh the fee to be charged according to the type of error and/or the frequency of occurrence. That is, the calculation unit 112 calculates a fee to be charged to the facility based on at least one of the type of error, the rank of error, and the frequency of error (frequency at which the cleaning machine 40 has not been used appropriately).

The calculation unit 112 stores the calculated fee to be charged and the facility information in the facility table 124 in association with each other. Caused by a user's operation, the output unit 14 outputs the fee to be charged and the facility information stored in the facility table 124 (S28).

As described above, according to the second embodiment, a fee to be charged for each facility can be calculated based on the error information related to the replacement of consumable items acquired from the cleaning machine 40. Therefore, a facility where the consumable items of the cleaning machine 40 are being appropriately replaced can reduce the maintenance cost of the cleaning machine 40.

Third Embodiment

Figure 6:
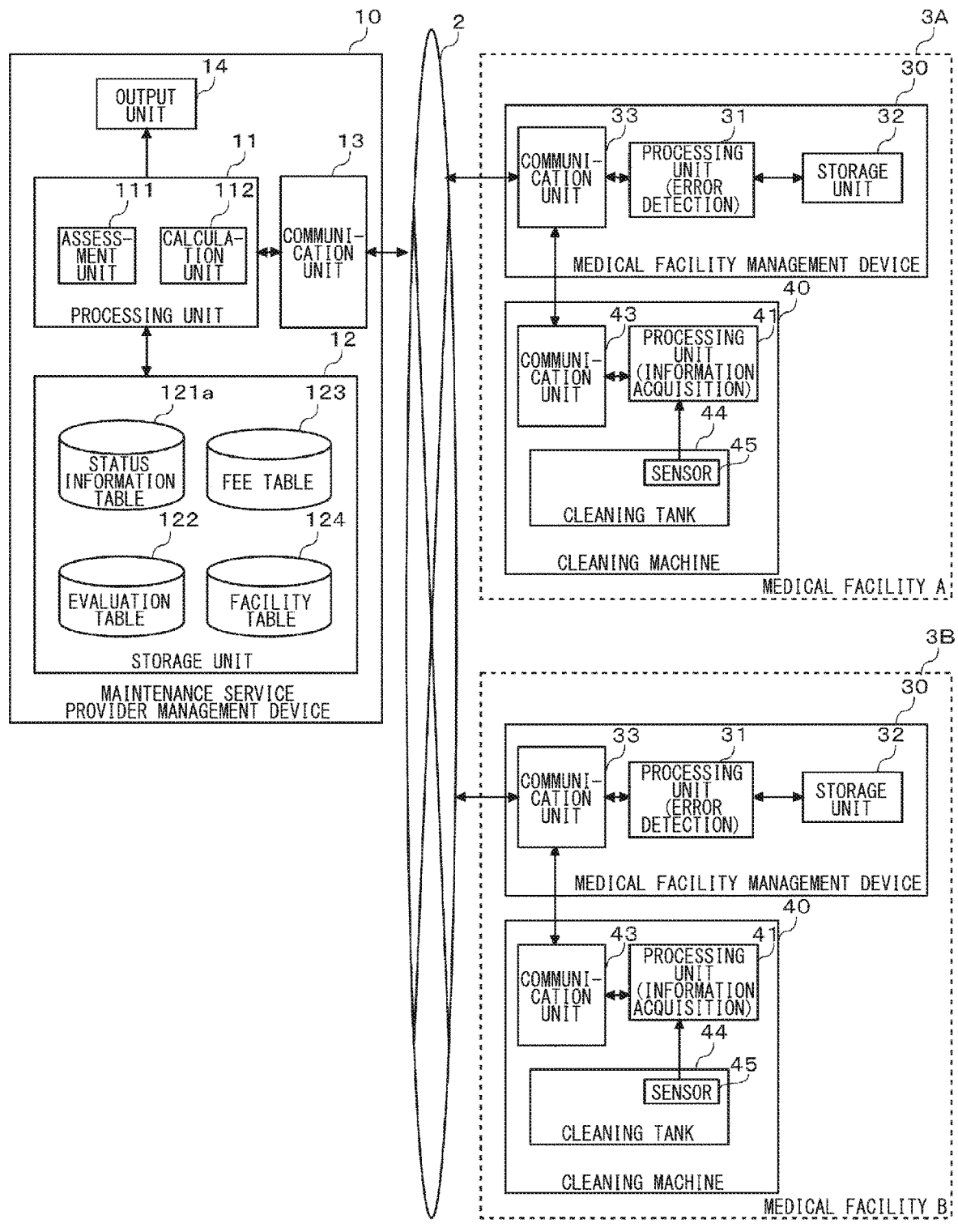
FIG. 6 is a block diagram showing the configuration of a fee-setting system according to the third embodiment of the present invention.

FIG. 6 is a block diagram showing the configuration of a fee-setting system 1 according to the third embodiment of the present invention. Compared with the second embodiment, the third embodiment is configured such that error detection related to the cleaning machine 40 is performed not by the processing unit 41 of the cleaning machine 40 but by the processing unit 31 of the medical facility management device 30. Further, a status information table 121a is provided instead of the error information table 121 of the storage unit 12 of the maintenance service provider management device 10.

Figure 7:
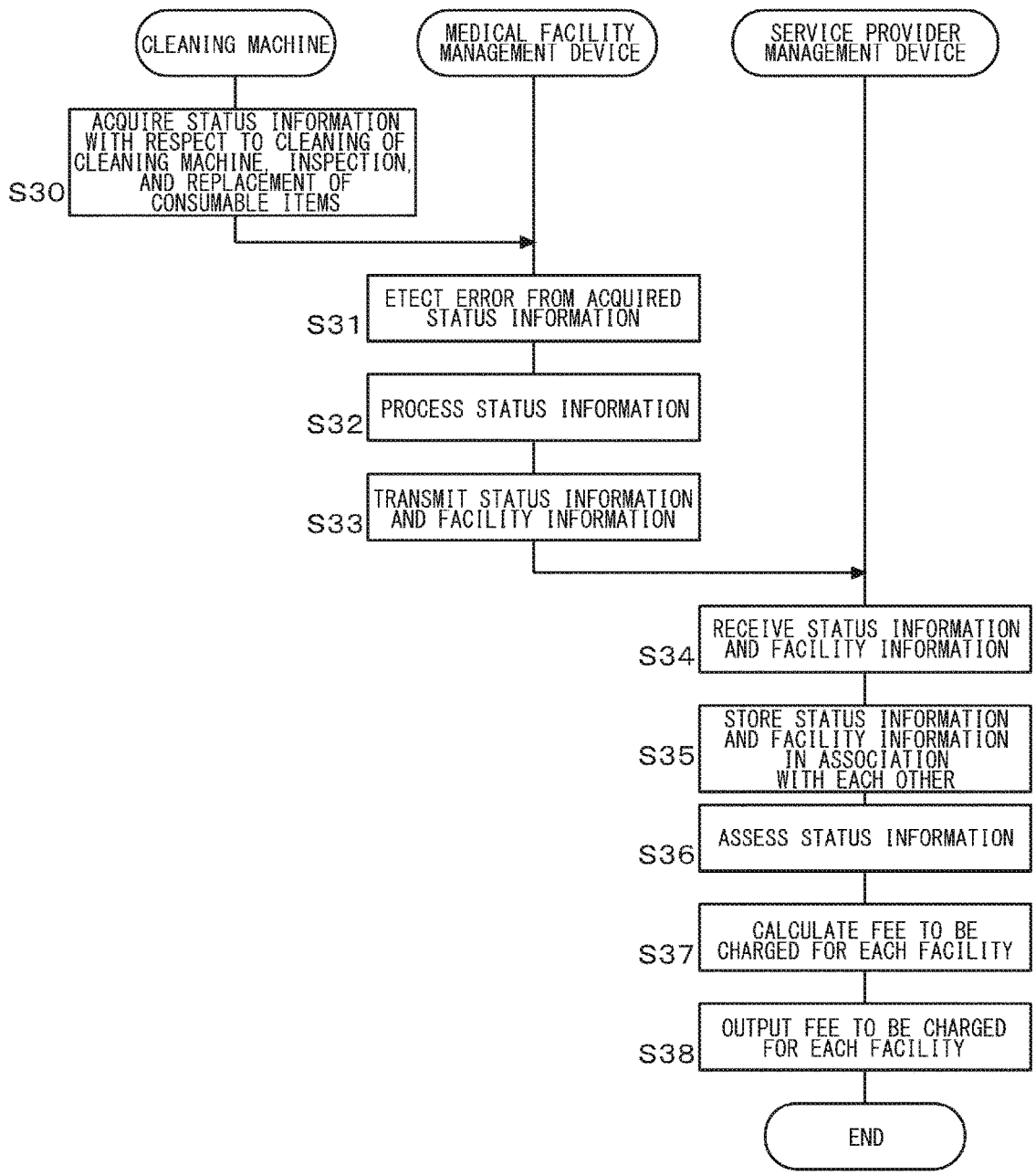
FIG. 7 is a flow chart showing the flow of a fee-setting process according to the third embodiment.

FIG. 7 is a flow chart showing the flow of a fee-setting process according to the third embodiment. The processing unit 41 of the cleaning machine 40 acquires status information with respect to the maintenance of the cleaning machine 40 (cleaning of the cleaning machine 40 itself, the inspection of the cleaning machine 40, the replacement of parts of the cleaning machine 40, and the replacement of consumable items) from various sensors in the cleaning machine 40 (S30). More specifically, the processing unit 41 acquires the use count of the consumable items, the number of elapsed days, the expiration date, the maintenance date of the cleaning machine 40, and a cleaning count (the total number of uses of the cleaning machine 40). The cleaning of the cleaning machine 40 includes, for example, the cleaning of a water supply tank, a cleaning tank, and a filter. The inspection of the cleaning machine 40 includes, for example, the inspection of a supply channel for water and cleaning solution, a drainage channel for water and cleaning solution, and a cleaning machine cover.

The processing unit 41 passes status information that has been acquired to the communication unit 43, and the communication unit 43 transmits the status information to the medical facility management device 30 via the internal network. The communication unit 33 of the medical facility management device 30 receives the status information from the cleaning machine 40 and passes the status information to the processing unit 31. The processing unit 31 detects an error related to the cleaning machine 40 based on the acquired status information (S31). More specifically, an error is detected if there is a consumable item that has exceeded a threshold value for the use count, the number of elapsed days, or the expiration date. Further, an error is detected if the maintenance date or the cleaning count of the cleaning machine 40 has exceeded a threshold value.

The processing unit 31 processes the status information after error detection (S32). The processing unit 31 adds the facility information regarding the medical facility to the processed status information and passes the processed status information to the communication unit 33. The communication unit 33 transmits the status information and the facility information to the maintenance service provider management device 10 via the external network 2 (S33). The status information is information reflecting the usage status of the cleaning machine 40.

The communication unit 13 of the maintenance service provider management device 10 receives the status information and the facility information via the external network 2 and passes the status information and the facility information to the processing unit 11 (S34). The processing unit 11 stores the status information and the facility information that have been received, in association with each other in the status information table 121a (S35).

At a predetermined timing, the assessment unit 111 reads the status information and the facility information stored in the status information table 121a and assesses the status information (S36). For example, by comparing the acquired value of a maintenance period calculated from the latest maintenance date and the previous maintenance date of the cleaning machine 40 with a reference value of a maintenance period of the cleaning machine 40, the assessment unit 111 can assess whether or not maintenance has been performed on the cleaning machine 40 at an appropriate time. Alternatively, by comparing the latest maintenance date of the cleaning machine 40 with a reference date for performing maintenance designated by the maintenance service provider, the assessment unit 111 may assess whether or not maintenance has been performed on the cleaning machine 40 at an appropriate time. Further, by comparing the acquired value of the cleaning count of the cleaning machine 40 with a reference value of the cleaning count of the cleaning machine 40, the assessment unit 111 can assess whether or not maintenance has been performed on the cleaning machine 40 at an appropriate time. The maintenance referred to in this case includes inspection and replacement of parts.

The assessment unit 111 can read evaluation reference information in the evaluation table 122, compare the status information and the evaluation reference information, and rank the degree of appropriateness regarding the use of the cleaning machine 40 based on the degree of deviation between the two.

FIG. 8 is a diagram showing an example of an evaluation table 122 according to the third embodiment. Evaluation items shown in FIG. 8 are the use count of a consumable item, the number of elapsed days of the consumable item, the expiration date of the consumable item, the maintenance date of a cleaning machine, the number of days elapsed before the cleaning by the cleaning machine, and the cleaning count of the cleaning machine. The evaluation on the use count of a consumable item is determined based on the ratio of consumable items that have been used within a standard count to all the consumable items. "Excellent" is given when the ratio is 90% or more, "Good" is given when the ratio is between 90% and 70%, "Fair" is given when the ratio is between 70% and 50%, and "Poor" is given when the ratio is 50% or less.

The evaluation of the number of elapsed days of the consumable item is determined based on the ratio of consumable items that have been used within the standard number of days to all the consumable items. The ranking method for the ratio is the same as that for the use count of the consumable item. The evaluation on the expiration date of the consumable item is determined based on the ratio of consumable items that have been replaced within the time limit to all the consumable items. The ranking method for the ratio is the same as that for the use count of the consumable item. The evaluation of the maintenance date of the cleaning machine is determined based on the ratio of cleaning machines that have not exceeded the maintenance time limit to all the cleaning machines. The ranking method for the ratio is the same as that for the use count of the consumable item. The evaluation on the number of days elapsed before the cleaning by the cleaning machine is determined based on the ratio of cleaning machines that have performed cleaning within a standard number of days to all the cleaning machines. The ranking method for the ratio is the same as that for the use count of the consumable item.

The evaluation on the cleaning count of the cleaning machine is determined based on the total number of cleanings performed since the introduction of the cleaning machine. "Excellent" is given when the total number of cleanings is within 5,000 times, "Good" is given when the total number of cleanings is between 5,000 and 10,000, "Fair" is given when the total number of cleanings is between 10,000 to 20,000, and "Poor" is given when the total number of cleanings is 20,000 or more.

FIG. 7 is referred back. The calculation unit 112 reads fee information regarding the usage status of the cleaning machine 40 and the usage status of the consumable item from the fee table 123. The calculation unit 112 calculates a fee to be charged for each medical facility based on the fee information that has been read, the assessment result by the assessment unit 111, and the facility information (S37). For example, the calculation unit 112 discounts, from the basic fee, the fee corresponding to the ratio of consumable items that have been used within a reference value and the ratio of cleanings performed while the cleaning machine was in an appropriately maintained condition, and calculate a final fee to be charged. At this time, the fee to be charged may be calculated in comparison with the degree of appropriateness regarding the use of the cleaning machine 40 ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S38).

As described above, according to the third embodiment, the fee to be charged for each facility can be calculated based on the status information with respect to the maintenance of the cleaning machine 40 acquired from the cleaning machine 40. Therefore, a facility where the cleaning machine 40 is appropriately used can reduce the maintenance cost of the cleaning machine 40.

A facility where not only a cleaning machine 40 but also a scope (not shown) is appropriately used can also reduce the maintenance cost of the scope. For example, by comparing the acquired value of a maintenance period calculated from the latest maintenance date and the previous maintenance date of the scope with a reference value of a maintenance period of the scope, the assessment unit 111 can assess whether or not maintenance has been performed on the scope at an appropriate time. Alternatively, by comparing the latest maintenance date of the scope with a reference date for performing maintenance designated by the maintenance service provider, the assessment unit 111 may assess whether or not maintenance has been performed on the scope at an appropriate time. Further, by comparing the acquired value of the use count of the scope with a reference value of the use count of the scope, the assessment unit 111 can assess whether or not maintenance has been performed on the scope at an appropriate time. The maintenance referred to in this case includes inspection and replacement of parts.

Fourth Embodiment

Figure 9:
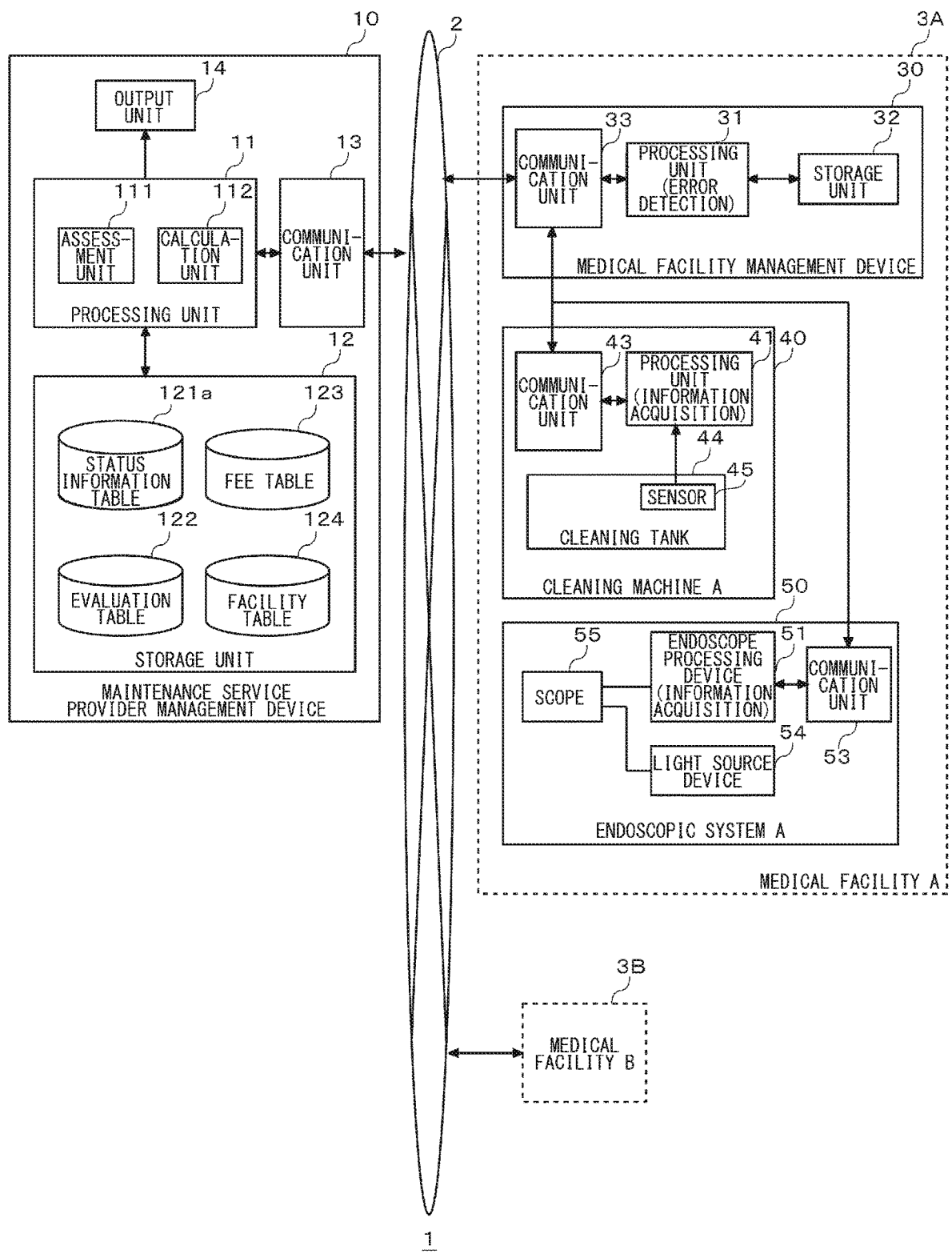
FIG. 9 is a block diagram showing the configuration of a fee-setting system according to the fourth embodiment of the present invention.

FIG. 9 is a block diagram showing the configuration of a fee-setting system 1 according to the fourth embodiment of the present invention. In the fourth embodiment, a medical facility management device 30, a cleaning machine 40, and an endoscopic system 50 are installed in each of the medical facility A (3A) and the medical facility B (3B).

The endoscopic system 50 includes a scope 55, an endoscope processing device 51, a light source device 54, and a communication unit 53. The scope 55 is inserted into the patient's body and images the inside of the patient's body. The scope 55 includes a solid-state imaging device (for example, CCD image sensor, CMD image sensor, or CMOS image sensor) and a signal processing circuit. The solid-state imaging device converts incident light into an electrical signal, and the signal processing circuit performs signal processing such as A/D conversion, noise removal, and the like on image data photoelectric-converted by the solid-state imaging device and outputs the resulting image data to the endoscope processing device 51. The light source device 54 includes a light source such as a xenon lamp or the like and transmits light to the distal end of the scope 55.

The endoscope processing device 51 acquires an image captured by the scope 55 and performs processing, displaying, recording, and the like of the image that has been acquired. The processing function of the endoscope processing device 51 can be realized by the cooperation of hardware resources and software resources or only by hardware resources. As the hardware resources, processors, ROM, RAM, and other LSIs can be used. A CPU, a GPU, and the like can be used as the processors. As the software resources, firmware and other programs can be used. The communication unit 53 executes a communication process that complies with a predetermined communication protocol. For example, the communication unit 43 executes a communication process with the medical facility management device 30 that complies with Ethernet (registered trademark).

Figure 10:
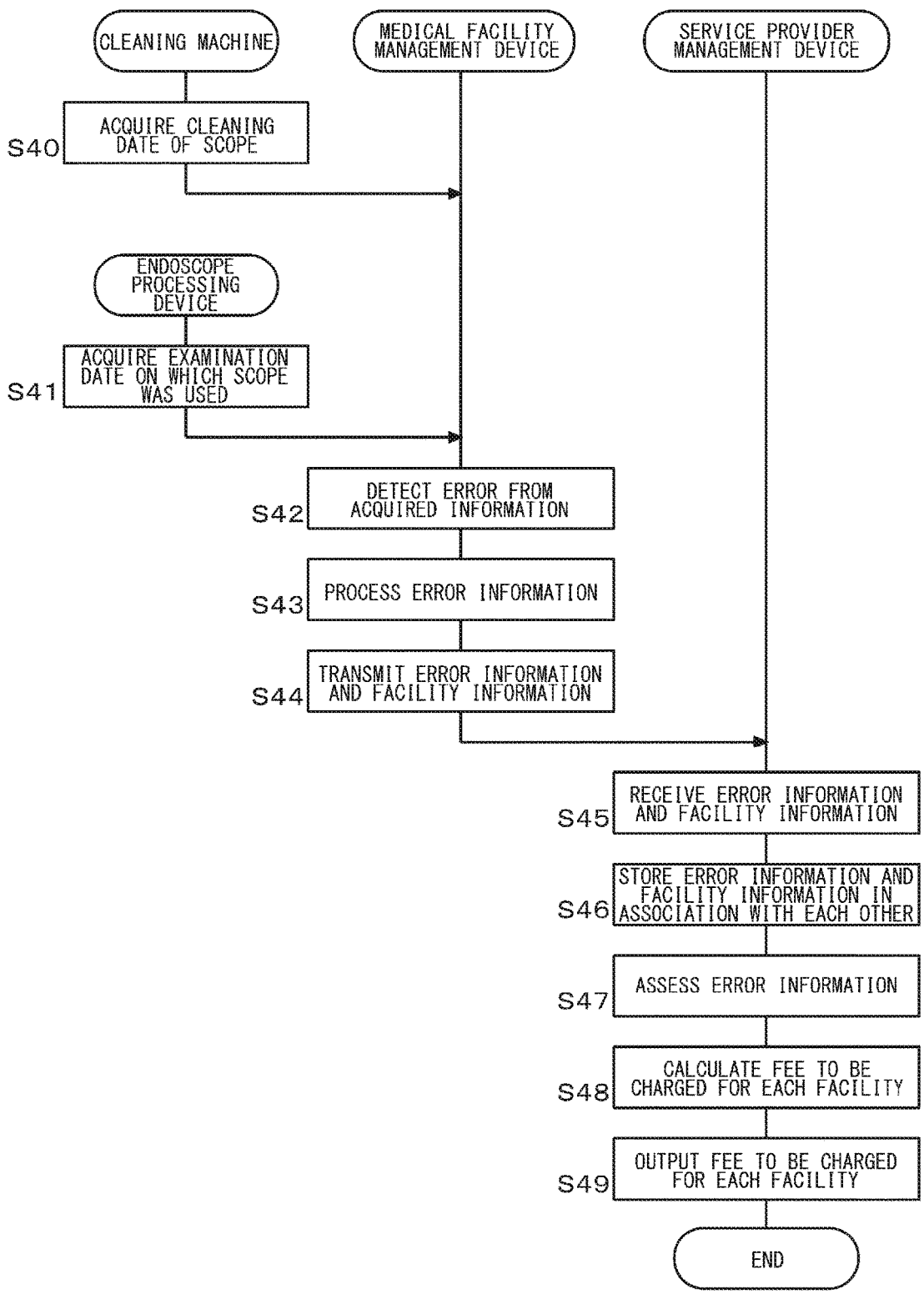
FIG. 10 is a flow chart showing the flow of a fee-setting process according to the fourth embodiment.

FIG. 10 is a flow chart showing the flow of a fee-setting process according to the fourth embodiment. The processing unit 41 of the cleaning machine 40 acquires the cleaning date of the scope (S40). A tag such as an RFID is attached to each scope. When starting cleaning using the cleaning machine 40, the cleaning person holds the tag of the scope over a reader (not shown) of the cleaning machine 40. The reader reads the scope ID from the tag of the scope. The processing unit 41 passes the scope ID and the cleaning date that have been read to the communication unit 43, and the communication unit 43 transmits the scope ID and the cleaning date of the scope including the scope ID to the medical facility management device 30 via the internal network.

The endoscope processing device 51 acquires the examination date of an endoscopy examination in which the scope 55 was used (S41). The endoscope processing device 51 has a function of identifying the scope ID of the scope 55 that has been inserted. The endoscope processing device 51 passes the identified scope ID and examination date to the communication unit 53, and the communication unit 53 transmits the scope ID and the examination date on which the scope including the scope ID was used to the medical facility management device 30 via the internal network.

The communication unit 33 of the medical facility management device 30 receives the cleaning date of the scope from the cleaning machine 40, receives the scope ID and the examination date on which the scope was used from the endoscopic system 50, and passes the cleaning date, the scope ID, and the examination date to the processing unit 31. The processing unit 31 detects an error related to the storage of the scope based on the scope ID, the cleaning date of the scope, and the examination date on which the scope was used that have been acquired (S42). More specifically, the processing unit 31 detects (1) the number of scopes whose storage time limit has passed since the last cleaning, (2) the number of scopes that have not been cleaned despite having being used for examinations until the previous day, and (3) the number of scopes used for examinations even though the time limit has passed.

The processing unit 31 processes the detected error information (S43). The processing unit 31 adds facility information regarding the medical facility to the processed error information and passes the processed error information to the communication unit 33. The communication unit 33 transmits the error information and the facility information to the maintenance service provider management device 10 via the external network 2 (S44).

The communication unit 13 of the maintenance service provider management device 10 receives the error information and the facility information via the external network 2 and passes the error information and the facility information to the processing unit 11 (S45). The processing unit 11 stores the error information and the facility information that have been received, in association with each other in the error information table 121 (S46).

At a predetermined timing, the assessment unit 111 reads the error information and the facility information stored in the error information table 121 and assesses the error information (S47). For example, by comparing the acquired value of the number of days from the use of the scope until the cleaning with a reference value of the number of days from the use of the scope until the cleaning, the assessment unit 111 can assess whether or not the scope was cleaned at an appropriate time. The number of days from the use of the scope until the cleaning can be obtained from the examination date on which the scope was used and the cleaning date of the scope.

The assessment unit 111 can read evaluation reference information in the evaluation table 122, compare the error information and the evaluation reference information, and rank the degree of appropriateness regarding the storage of the scope based on the degree of deviation between the two.

FIG. 11 is a diagram showing an example of an evaluation table 122 according to the fourth embodiment. Evaluation items shown in FIG. 11 are a scope with an expired storage time limit, time until the cleaning of a scope after the examination, and an examination in which a scope with an expired storage time limit was used. The evaluation on a scope with an expired storage time limit is determined based on the ratio of stored scopes with an expired storage time limit to all the scopes stored in the medical facility. "Excellent" is given when the ratio is 10% or less, "Good" is given when the ratio is between 10% and 30%, "Fair" is given when the ratio is between 30% and 50%, and "Poor" is given when the ratio is 50% or more.

Evaluation on the time until the cleaning of a scope after the examination is determined based on the ratio of the scopes that are left uncleaned for more than the reference time after the examination to all the scopes stored in the medical facility. The ranking method for the ratio is the same as that for the scopes with an expired storage time limit. The evaluation on the examination in which a scope with an expired storage time limit was used is determined based on the number of examinations in which a scope with an expired storage time limit was used. "Excellent" is given when the number is 0, and "Poor" is given when the number is 1 or more.

FIG. 10 is referred back. The calculation unit 112 reads fee information with respect to a storage error of a scope from the fee table 123. In comparison with the fee information that has been read and the degree of appropriateness regarding the storage of the scope that has been ranked, the calculation unit 112 calculates a fee to be charged (for example, a maintenance fee) for each facility based on the assessment result by the assessment unit 111 and the facility information (S48). For example, the calculation unit 112 discounts, from the basic fee, the fee corresponding to the ratio of stored scopes with an expired storage time limit, the ratio of the scopes left uncleaned, and the number of examinations in which a scope with an expired storage time limit was used, and calculate a final fee to be charged. At this time, the fee to be charged may be calculated in comparison with the degree of appropriateness regarding the storage of the scope ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S49).

As described above, according to the fourth embodiment, a fee to be charged for each facility can be calculated based on the error information related to the storage of the scope acquired from the cleaning machine 40 and the endoscope processing device 51. Therefore, a facility where a scope is appropriately stored can reduce the maintenance cost of the scope.

Although a scope including an imaging device has been described above, the scope does not necessarily include an image device, and a camera head connected to a rigid video scope, a fiber scope, or the like may include an image sensor.

By comparing the number of days passed from the use to the cleaning with a reference value not just for a scope but for a treatment tool such as a clip or a treatment device that cuts or seals blood vessels, mucous membranes, and the like using thermal energy or ultrasonic energy, whether or not the treatment tool or the treatment device has been cleaned at an appropriate time can be assessed.

Exemplary Variation of Fourth Embodiment

Figure 12:
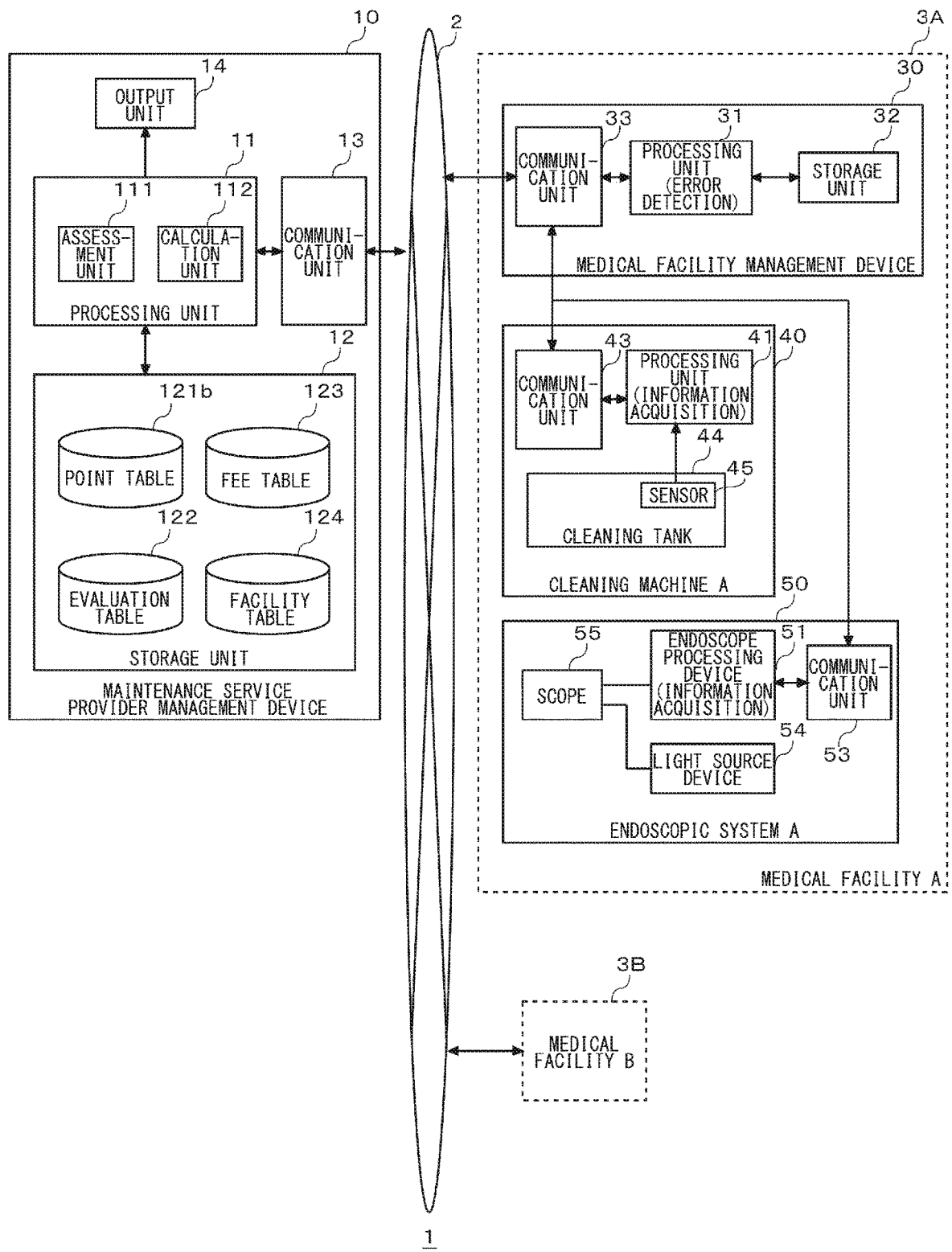
FIG. 12 is a block diagram showing the configuration of a fee-setting system according to an exemplary variation of the fourth embodiment of the present invention.

FIG. 12 is a block diagram showing the configuration of a fee-setting system 1 according to an exemplary variation of the fourth embodiment of the present invention. In the exemplary variation of the fourth embodiment, a point table 121b is provided instead of the error information table 121 of the storage unit 12 of the maintenance service provider management device 10.

Figure 13:
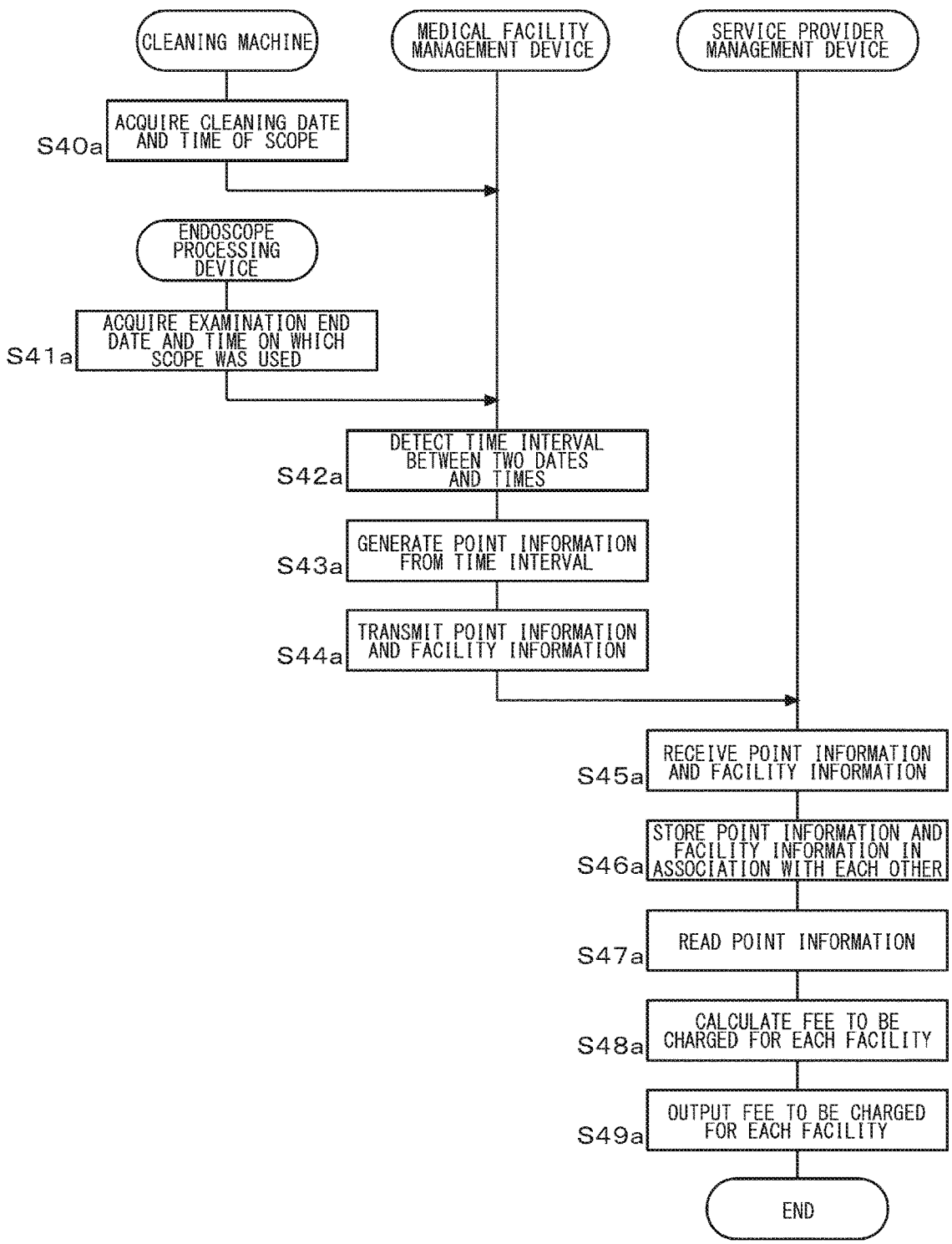
FIG. 13 is a flow chart showing the flow of a fee-setting process according to an exemplary variation of the fourth embodiment.

FIG. 13 is a flow chart showing the flow of a fee-setting process according to an exemplary variation of the fourth embodiment. The processing unit 41 of the cleaning machine 40 acquires the cleaning date and time of a scope (S40a). The processing unit 41 passes the scope ID and cleaning date and time of the scope to the communication unit 43, and the communication unit 43 transmits the scope ID and the cleaning date and time of the scope including the scope ID to the medical facility management device 30 via the internal network.

The endoscope processing device 51 acquires the examination date and time of an endoscopy examination in which the scope 55 was used (S41a). The endoscope processing device 51 can detect the examination end date and time based on the time when dimming sensing data becomes a predetermined value or less. When the distal end of the scope 55 is moved out of the body, the distance between the solid-state imaging device in the scope 55 and the subject becomes longer, and the dimming sensing data therefore becomes smaller. The dimming sensing data is data used to determine the light amount of the light source device 54. The endoscope processing device 51 passes the scope ID and examination end date and time of the scope used in the examination to the communication unit 53, and the communication unit 53 transmits the scope ID and the examination end date and time at which the scope including the scope ID was used to the medical facility management device 30 via the internal network.

The communication unit 33 of the medical facility management device 30 receives the scope ID and the cleaning date and time of the scope from the cleaning machine 40, receives the scope ID and the end date and time of the examination in which the scope was used from the endoscopic system 50, and passes the scope ID, the cleaning date and time, and the end date and time of the examination to the processing unit 31. The processing unit 31 detects a time interval between the cleaning date and time of the scope and the end date and time of the examination in which the scope was used that have been acquired (S42). The processing unit 31 processes the detected time interval (S43a). For example, if the detected time interval is a predetermined value or less, the processing unit 31 adds bonus points to the basic points.

The processing unit 31 adds facility information regarding the medical facility to the processed point information and passes the processed point information to the communication unit 33. The communication unit 33 transmits the point information and the facility information to the maintenance service provider management device 10 via the external network 2 (S44a). The point information is information reflecting the usage status of the scope. The communication unit 13 of the maintenance service provider management device 10 receives the point information and the facility information via the external network 2 and passes the point information and the facility information to the processing unit 11 (S45a). The processing unit 11 stores the point information and the facility information that have been received, in association with each other in the point table 121b (S46a).

At a predetermined timing, the assessment unit 111 reads the point information and the facility information stored in the point table 121b (S47a). The calculation unit 112 reads fee information corresponding to the point information from the fee table 123. In comparison with the fee information that has been read and the point information, the calculation unit 112 calculates a fee to be charged for each medical facility (S48a). The calculation unit 112 stores the calculated fee to be charged and the facility information in the facility table 124 in association with each other. Caused by a user's operation, the output unit 14 outputs the fee to be charged and the facility information stored in the facility table 124 (S49a).

As described above, according to the exemplary variation of the fourth embodiment, a fee to be charged for each facility can be calculated based on the time interval between a cleaning start date and time acquired from the cleaning machine 40 and the examination end date and time acquired from the endoscope processing device 51. Therefore, a facility where a scope is cleaned without delay after the examination is ended can reduce the maintenance cost of the scope.

Fifth Embodiment

Figure 14:
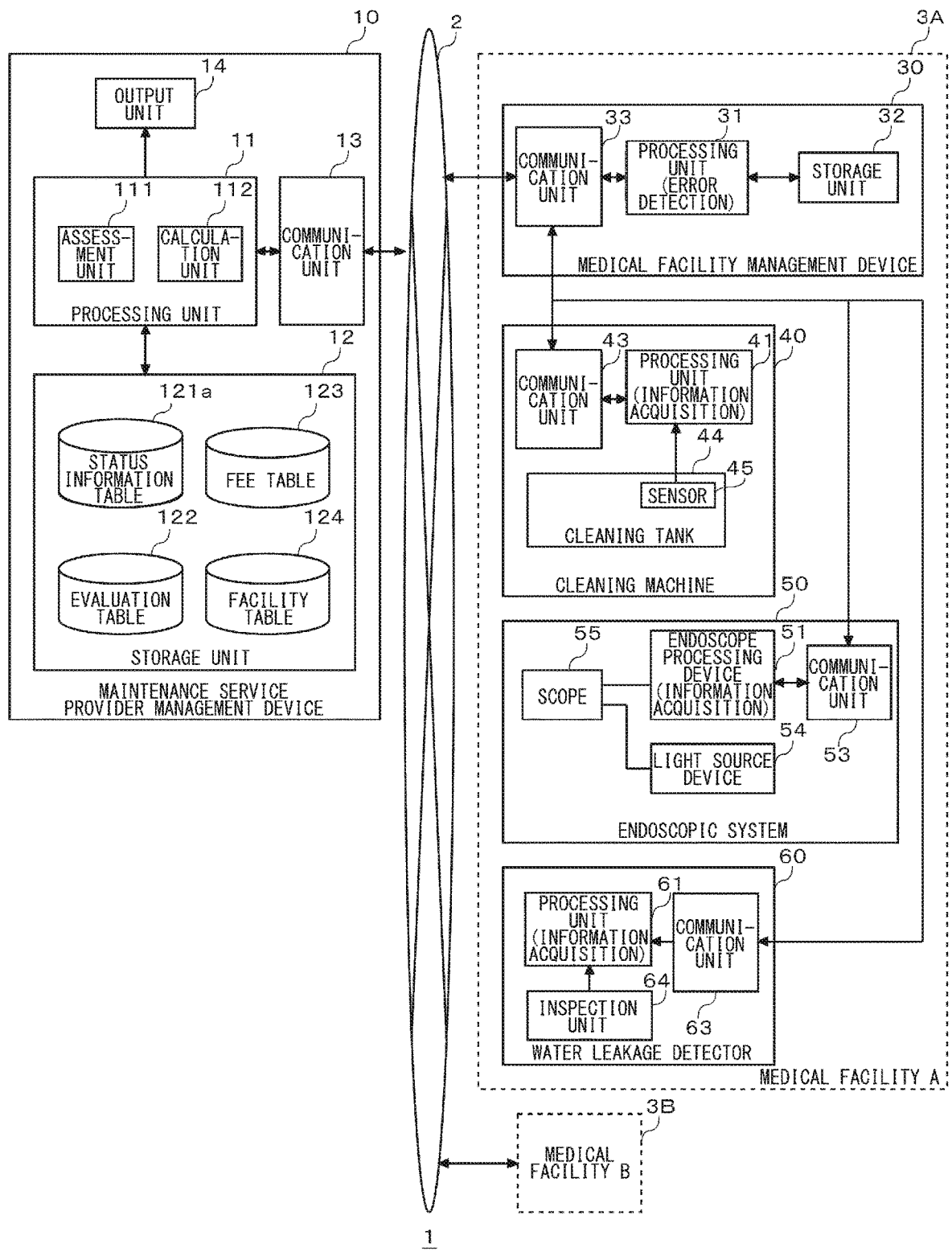
FIG. 14 is a block diagram showing the configuration of a fee-setting system according to the fifth embodiment of the present invention.

FIG. 14 is a block diagram showing the configuration of a fee-setting system 1 according to the fifth embodiment of the present invention. In the fifth embodiment, a medical facility management device 30, a cleaning machine 40, an endoscopic system 50, and a water leakage detector 60 are installed in each of the medical facility A (3A) and the medical facility B (3B). The water leakage detector 60 is a device for inspecting for water leakage in a scope. The water leakage inspection is an inspection for checking whether the waterproof function of the scope is secured. The water leakage detector 60 includes a processing unit 61, a communication unit 63, and an inspection unit 64. For example, whether there is water leakage is detected by immersing the scope in water while the scope is being attached to the inspection unit 64 and then checking whether or not bubbles are generated from the scope.

The processing unit 61 can be realized by the cooperation of hardware resources and software resources or only by hardware resources. As the hardware resources, processors, ROM, RAM, and other LSIs can be used. As the processors, microcomputers, DSPs, FPGAs, and the like can be used. As the software resources, firmware and other programs can be used. The communication unit 63 executes a communication process that complies with a predetermined communication protocol. For example, the communication unit 43 executes a communication process with the medical facility management device 30 that complies with Ethernet (registered trademark).

Figure 15:
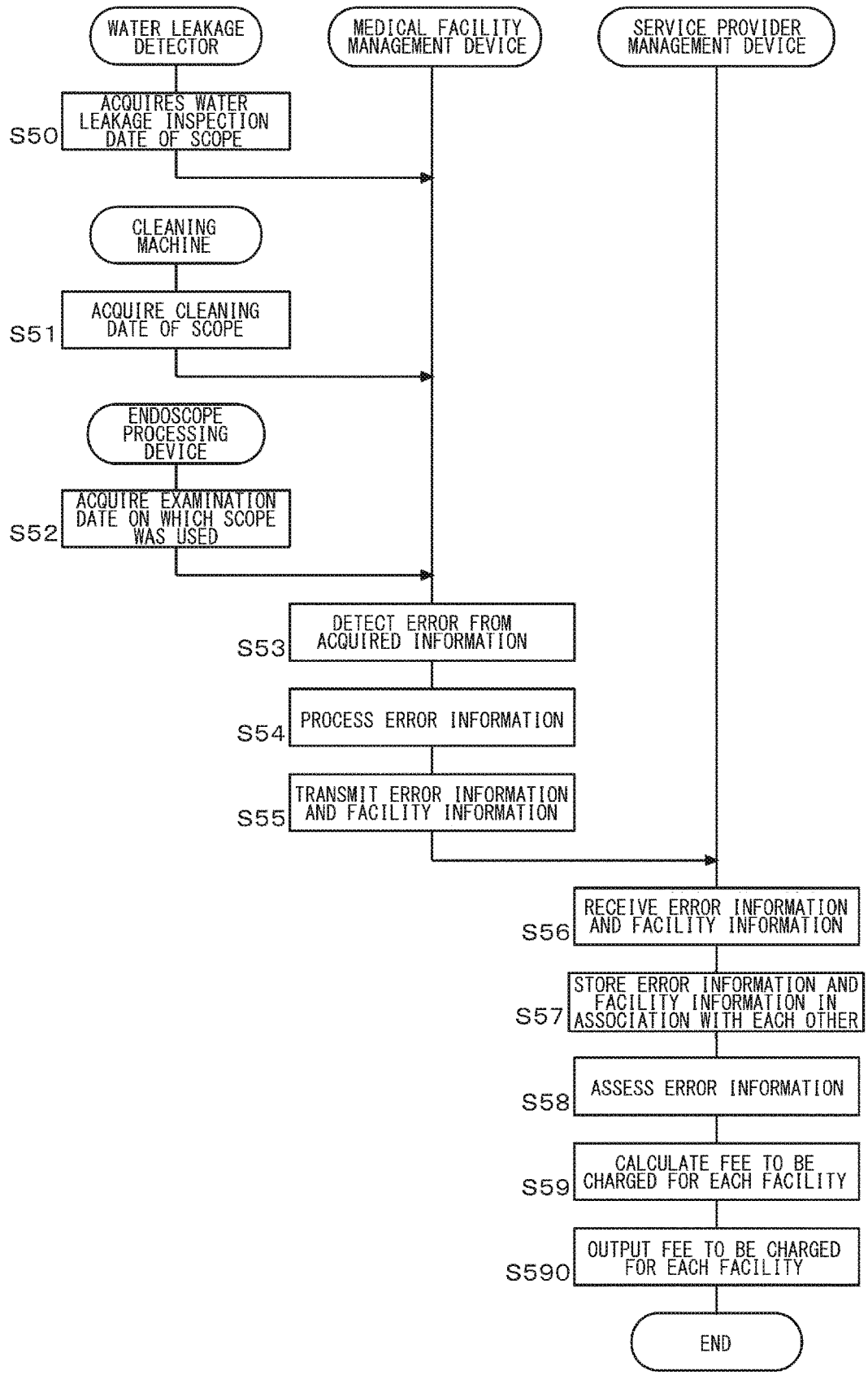
FIG. 15 is a flow chart showing the flow of a fee-setting process according to the fifth embodiment.

FIG. 15 is a flow chart showing the flow of a fee-setting process according to the fifth embodiment. The processing unit 61 of the water leakage detector 60 acquires a water leakage inspection date of the scope (S50). As described above, a tag such as an RFID is attached to each scope, and a scope ID is stored in the tag. The inspector holds the tag of the scope over a reader (not shown) of the water leakage detector 60 when starting water leakage inspection of the scope using the water leakage detector 60. The reader reads the scope ID from the tag of the scope. The processing unit 61 passes the scope ID and the water leakage inspection date that have been read to the communication unit 63, and the communication unit 63 transmits the scope ID and the water leakage inspection date of the scope including the scope ID to the medical facility management device 30 via the internal network.

The processing unit 41 of the cleaning machine 40 acquires the cleaning date of the scope (S51). The processing unit 41 passes the scope ID and cleaning date of the scope that has been cleaned to the communication unit 43, and the communication unit 43 transmits the scope ID and the cleaning date of the scope including the scope ID to the medical facility management device 30 via the internal network.

The endoscope processing device 51 acquires the examination date of an examination in which the scope 55 was used (S52). The endoscope processing device 51 passes the scope ID and examination date of the scope 55 that has been used to the communication unit 53, and the communication unit 53 transmits the scope ID and the examination date of the examination in which the scope including the scope ID was used to the medical facility management device 30 via the internal network.

The communication unit 33 of the medical facility management device 30 receives the scope ID and the water leakage inspection date of the scope from the water leakage detector 60, receives the scope ID and the cleaning date of the scope from the cleaning machine 40, receives the scope ID and the examination date of the examination in which the scope was used from the endoscopic system 50, and passes the scope ID, the water leakage inspection date, the cleaning date, and the examination date to the processing unit 31. The processing unit 31 detects an error related to the storage of the scope based on the scope ID, the water leakage inspection date of the scope, the cleaning date of the scope, and the examination date of the examination in which the scope was used that have been acquired (S53). More specifically, the processing unit 31 detects (1) the number of scopes whose storage time limit has passed since the last cleaning, (2) the number of scopes that have not been cleaned despite having being used for examinations until the previous day, (3) the number of scopes used for examinations even though the time limit has passed, (4) the number of scopes for which water leakage inspection has not been performed, and (5) the number of scopes used in an examination even after the detection of water leakage.

The processing unit 31 processes error information of a scope that has been detected (S54). The processing unit 31 adds facility information regarding the medical facility to the processed error information and passes the processed error information to the communication unit 33. The communication unit 33 transmits the error information and the facility information to the maintenance service provider management device 10 via the external network 2 (S55).

The communication unit 13 of the maintenance service provider management device 10 receives the error information and the facility information via the external network 2 and passes the error information and the facility information to the processing unit 11 (S56). The processing unit 11 stores the error information and the facility information that have been received, in association with each other in the error information table 121 (S57).

At a predetermined timing, the assessment unit 111 reads the error information and the facility information stored in the error information table 121 and assesses the error information (S58). For example, by comparing the acquired value of the number of days from the use of the scope until the water leakage inspection with a reference value of the number of days from the use of the scope until the water leakage inspection, the assessment unit 111 can assess whether or not water leakage inspection has been performed on the scope at an appropriate time. The number of days from the use of the scope until the water leakage inspection can be obtained based on the examination date of the examination in which the scope was used and the water leakage inspection date of the scope.

Further, by comparing the order of the water leakage inspection date of the scope, the maintenance date of the scope, and the examination date of the examination in which the scope was used with a scope usage standard used when water leakage is detected, the assessment unit 111 can assess whether or not the scope has been used appropriately.

Further, the assessment unit 111 can read evaluation reference information in the evaluation table 122, compare the error information and the evaluation reference information, and rank the degree of appropriateness regarding the storage of the scope based on the degree of deviation between the two.

FIG. 16 is a diagram showing an example of an evaluation table 122 according to the fifth embodiment. Evaluation items shown in FIG. 16 represent a scope whose storage time limit has passed since the last cleaning, a scope that has not been cleaned despite having being used for an examination until the previous day, a scope used for an examination even though the storage time limit has passed, a scope for which water leakage inspection has not been performed, and a scope used in an examination even after the detection of water leakage.

The evaluation on a scope whose storage time limit has passed is determined based on the ratio of scopes that have been stored within a storage time limit to all the scopes stored in the medical facility. "Excellent" is given when the ratio is 90% or more, "Good" is given when the ratio is between 90% and 70%, "Fair" is given when the ratio is between 70% and 50%, and "Poor" is given when the ratio is 50% or less.

The evaluation on a scope that has not been cleaned despite having been used in an examination until the previous day is determined based on the ratio of scopes that have been cleaned by the following day after the examination to all scopes stored in medical facility. The ranking method for the ratio is the same as that for the scope whose storage time limit has passed since the last cleaning. The evaluation on a scope used for an examination even though the storage time limit has passed is determined based on the number of scopes used for an examination even after the expiration of the storage time limit. "Excellent" is given when the number is 0, and "Poor" is given when the number is 1 or more.

The evaluation on a scope for which water leakage inspection has not been performed is determined based on the ratio of the number of scopes for which water leakage inspection has not been performed to the total number of scopes for which water leakage inspection has been performed after the examination. The ranking method for the ratio is the same as that for the scope whose storage time limit has passed since the last cleaning. The evaluation on a scope used in an examination even after the detection of water leakage is determined based on the number of scopes used in an examination even after the detection of water leakage. "Excellent" is given when the number is 0, and "Poor" is given when the number is 1 or more.

FIG. 15 is referred back. The calculation unit 112 reads fee information with respect to a storage error of a scope from the fee table 123. The calculation unit 112 calculates a fee to be charged (for example, a maintenance fee) for each facility based on the fee information that has been read, the assessment result by the assessment unit 111, and the facility information (S59). For example, the calculation unit 112 discounts, from the basic fee, the fee corresponding to the ratio of the number of scopes for which water leakage inspection has not been performed and the number of scopes used in an examination even after the detection of water leakage and calculate a final fee to be charged. At this time, the fee to be charged may be calculated in comparison with the degree of appropriateness regarding the storage of the scope ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S510).

As described above, according to the fifth embodiment, a fee to be charged for each facility can be calculated based on the error information regarding the storage of the scope acquired from the water leakage detector 60, the cleaning machine 40, and the endoscope processing device 51. Therefore, a facility where a scope is appropriately stored can reduce the maintenance cost of the scope.

In FIG. 14, an example in which the water leakage detector 60 is a dedicated machine has been described. However, if the cleaning machine 40 is equipped with a water leakage detection function, water leakage inspection of a scope may be performed using the water leakage detection function of the cleaning machine 40. In that case, the water leakage inspection date of the scope is acquired from the cleaning machine 40 instead of the water leakage detector 60. For example, a scope used in an endoscopic examination is set in the cleaning machine 40 and detected based on log information of a water leakage detection operation switch (not shown) indicating that water leakage inspection has been performed.

Sixth Embodiment

Figure 17:
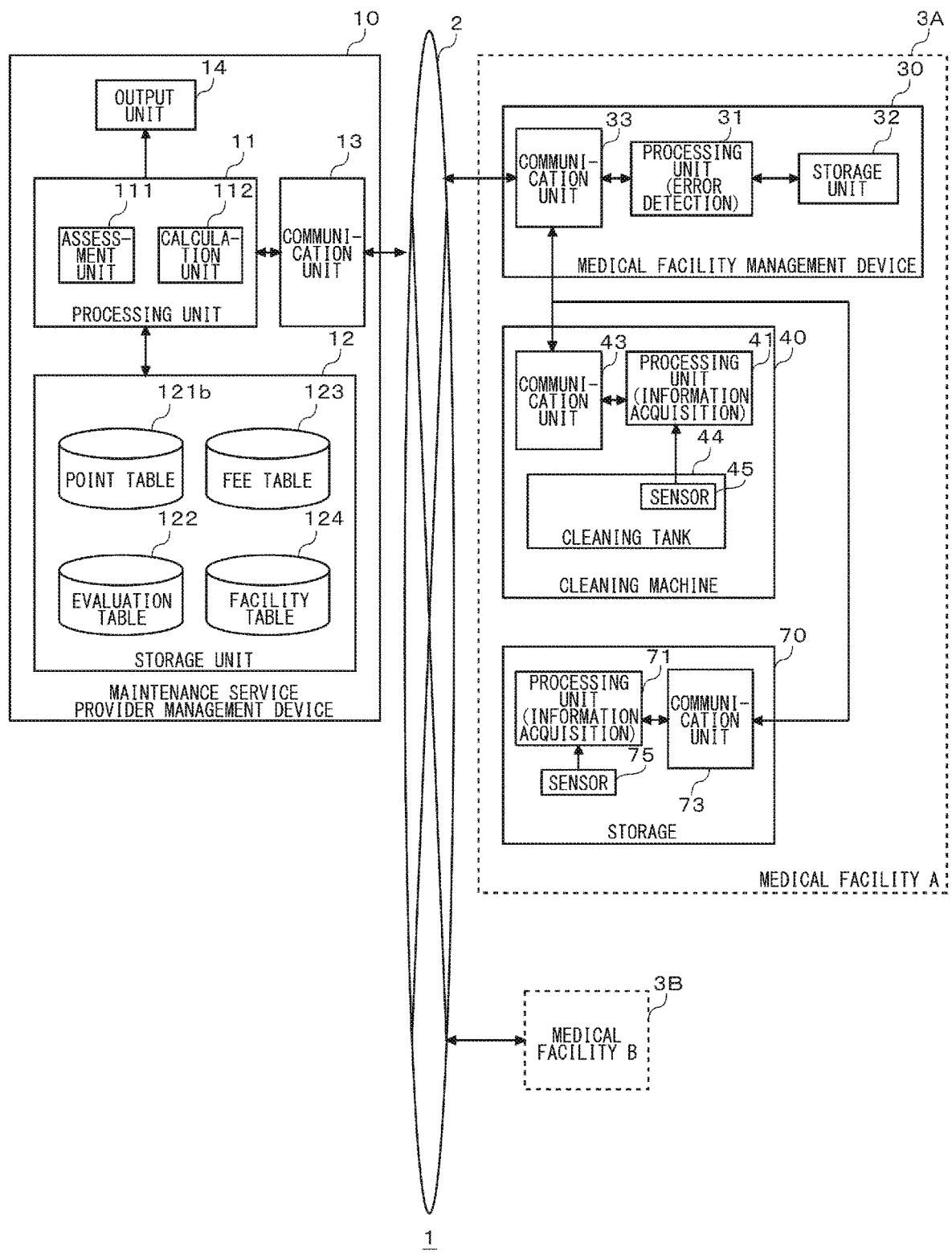
FIG. 17 is a block diagram showing the configuration of a fee-setting system according to the sixth embodiment of the present invention.

FIG. 17 is a block diagram showing the configuration of a fee-setting system 1 according to the sixth embodiment of the present invention. In the sixth embodiment, a medical facility management device 30, a cleaning machine 40, and a storage 70 are installed in each of the medical facility A (3A) and the medical facility B (3B). The storage 70 is a storage for storing scopes. The inside of the storage is kept at low temperature and low humidity in order to prevent fungal growth. The storage 70 includes a processing unit 71, a communication unit 73, and a sensor 75. The sensor 75 is a general term for a plurality of sensors for detecting whether or not a scope exists at each storage position of the storage 70. The sensor 75 also has a function of reading a scope ID embedded in a tag of the scope.

The processing unit 71 can be realized by the cooperation of hardware resources and software resources or only by hardware resources. As the hardware resources, processors, ROM, RAM, and other LSIs can be used. As the processors, microcomputers, DSPs, FPGAs, and the like can be used. As the software resources, firmware and other programs can be used. The communication unit 73 executes a communication process that complies with a predetermined communication protocol. For example, the communication unit 43 executes a communication process with the medical facility management device 30 that complies with Ethernet (registered trademark).

Figure 18:
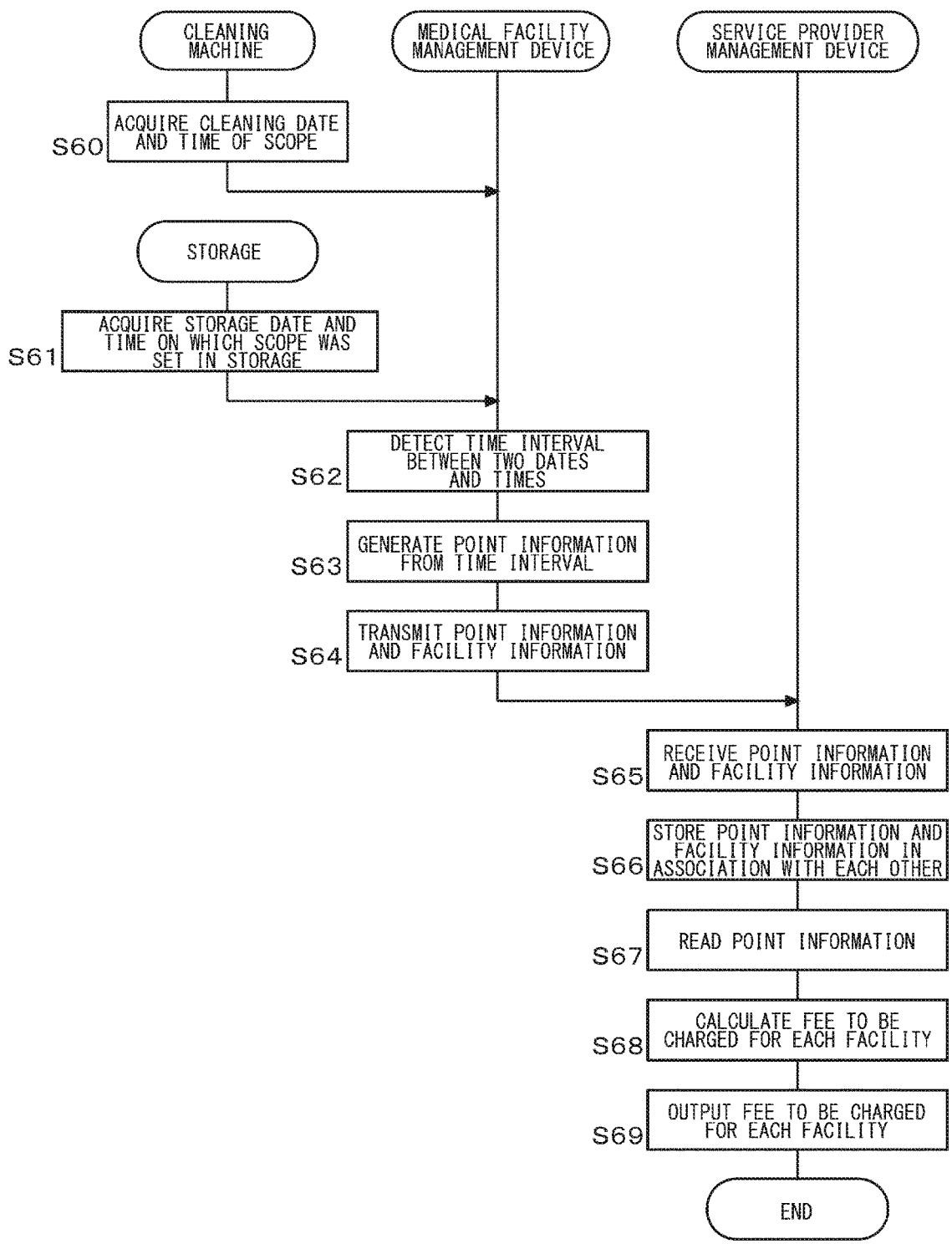
FIG. 18 is a flow chart showing the flow of a fee-setting process according to the sixth embodiment.

FIG. 18 is a flow chart showing the flow of a fee-setting process according to the sixth embodiment. The processing unit 41 of the cleaning machine 40 acquires the cleaning date and time of the scope (S60). The processing unit 41 passes the scope ID and cleaning date and time of the scope to the communication unit 43, and the communication unit 43 transmits the scope ID and the cleaning date and time of the scope including the scope ID to the medical facility management device 30 via the internal network.

The processing unit 71 of the storage 70 acquires the storage date and time when the scope was set at a predetermined position in the storage (S61). The processing unit 71 passes the scope ID and storage date and time of the scope to the communication unit 73, and the communication unit 73 transmits the scope ID and the storage date and time of the scope including the scope ID to the medical facility management device 30 via the internal network.

The communication unit 33 of the medical facility management device 30 receives the scope ID and the cleaning date and time of the scope from the cleaning machine 40, receives the scope ID and the storage date and time of the scope from the storage 70, and passes the scope ID, the cleaning date and time, and the storage date and time of the scope to the processing unit 31. The processing unit 31 detects a time interval between the cleaning date and time of the scope and the storage date and time of the scope that have been acquired (S62). The processing unit 31 processes the detected time interval (S63). For example, if the detected time interval is a predetermined value or less, the processing unit 31 adds bonus points to the basic points.

The processing unit 31 adds facility information regarding the medical facility to the processed point information and passes the processed point information to the communication unit 33. The communication unit 33 transmits the point information and the facility information to the maintenance service provider management device 10 via the external network 2 (S64). The communication unit 13 of the maintenance service provider management device 10 receives the point information and the facility information via the external network 2 and passes the point information and the facility information to the processing unit 11 (S65). The processing unit 11 stores the point information and the facility information that have been received, in association with each other in the point table 121b (S66).

At a predetermined timing, the assessment unit 111 reads the point information and the facility information stored in the point table 121b (S67). The calculation unit 112 reads fee information corresponding to the point information from the fee table 123. In comparison with the fee information that has been read and the point information, the calculation unit 112 calculates a fee to be charged for each medical facility (S68). The calculation unit 112 stores the calculated fee to be charged and the facility information in the facility table 124 in association with each other. Caused by a user's operation, the output unit 14 outputs the fee to be charged and the facility information stored in the facility table 124 (S69).

As described above, according to the sixth embodiment, a fee to be charged for each facility can be calculated based on the time interval between a cleaning start date and time acquired from the cleaning machine 40 and the storage date and time acquired from the storage 70. Therefore, a facility where a scope is stored in a storage without delay after the cleaning is ended can reduce the maintenance cost of the scope.

Based on the status information without using the point information, by comparing the acquired value of the number of days from when the scope started being stored in the storage 70 until when the scope was used with a reference value of the number of days from when a scope starts being stored in the storage 70 until when the scope is used, the assessment unit 111 may assess whether or not the scope has been used at an appropriate time.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

In the above-described embodiment, the example has been described in which the process of assessing error information and the process of calculating maintenance fee are performed by the maintenance service provider management device 10. A maintenance service provider management device 10 is constructed and operated by the system department of the maintenance service provider. In the exemplary variation described below, an example will be described in which part or all of the functions of the maintenance service provider management device 10 are outsourced to a cloud service provider. Thereby, the system construction cost and system operation cost of the maintenance service provider can be reduced. In the following exemplary variation, an exemplary variation based on the configuration according to the second embodiment will be described. The configurations according to the first and third through sixth embodiments can be modified in the same way.

First Exemplary Variation

Figure 19:
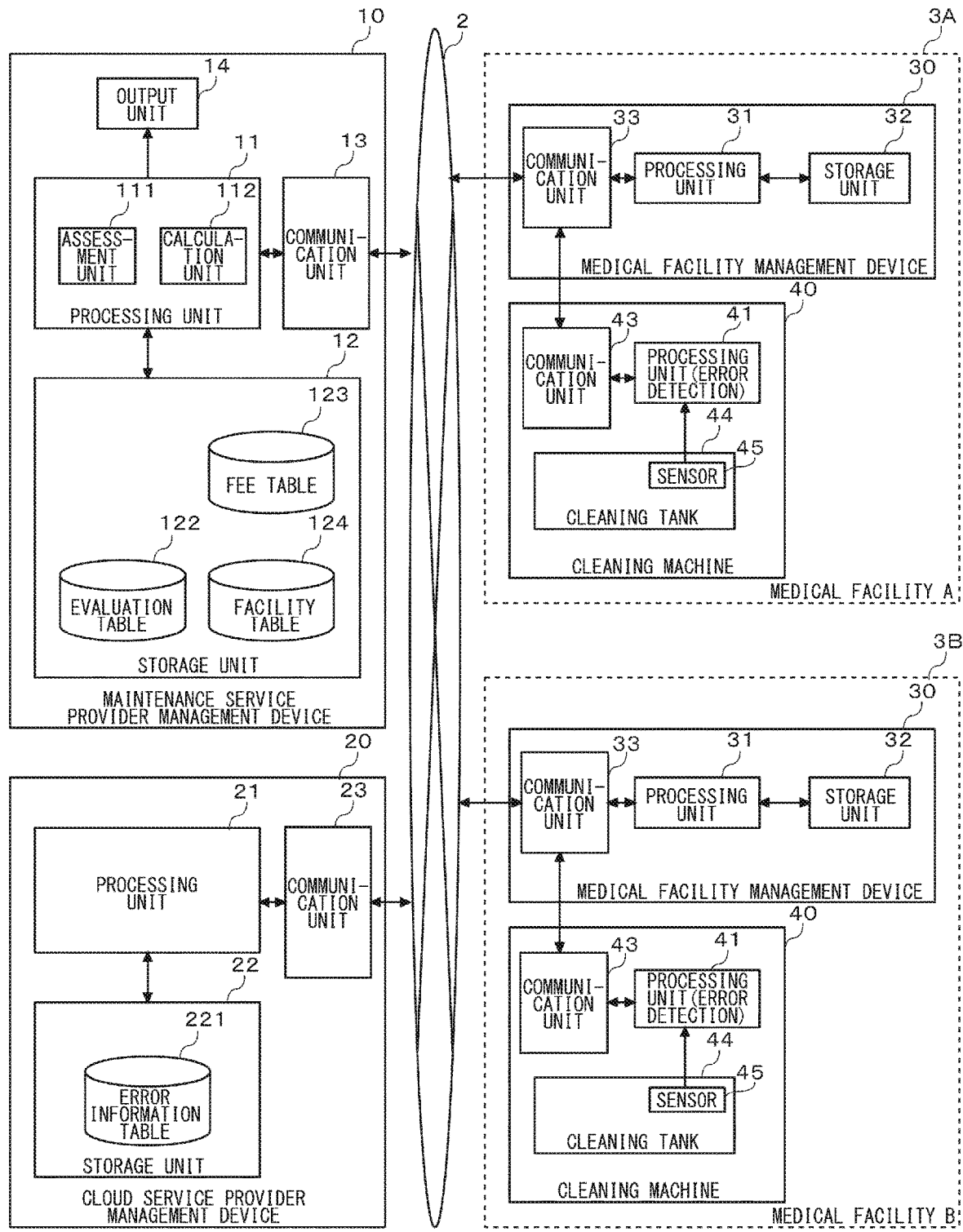
FIG. 19 is a block diagram showing the configuration of a fee-setting system according to the first exemplary variation of the present invention.

FIG. 19 is a block diagram showing the configuration of a fee-setting system 1 according to the first exemplary variation of the present invention. A cloud service provider includes a cloud service provider management device 20. The cloud service provider management device 20 is constructed with a plurality of servers and peripheral devices. The cloud service provider management device 20 includes a processing unit 21, a storage unit 22, and a communication unit 23.

The processing unit 21 can be realized by the cooperation of hardware resources and software resources or only by hardware resources. As the hardware resources, processors, ROM, RAM, and other LSIs can be used. A CPU, a GPU, and the like can be used as the processors. Programs such as operating systems and applications can be used as the software resources. The storage unit 22 includes a non-volatile recording medium such as HDD, SSD, etc. The communication unit 23 executes a communication process that complies with a predetermined communication protocol. For example, the communication unit 23 executes communication processes with the maintenance service provider management device 10, the medical facility management device 30 of the medical facility A (3A) and the medical facility management device 30 of the medical facility B (3B) that complies with Ethernet (registered trademark).

In the first exemplary variation, an error information table 221 is constructed in the storage unit 22 of the cloud service provider management device 20.

Figure 20:
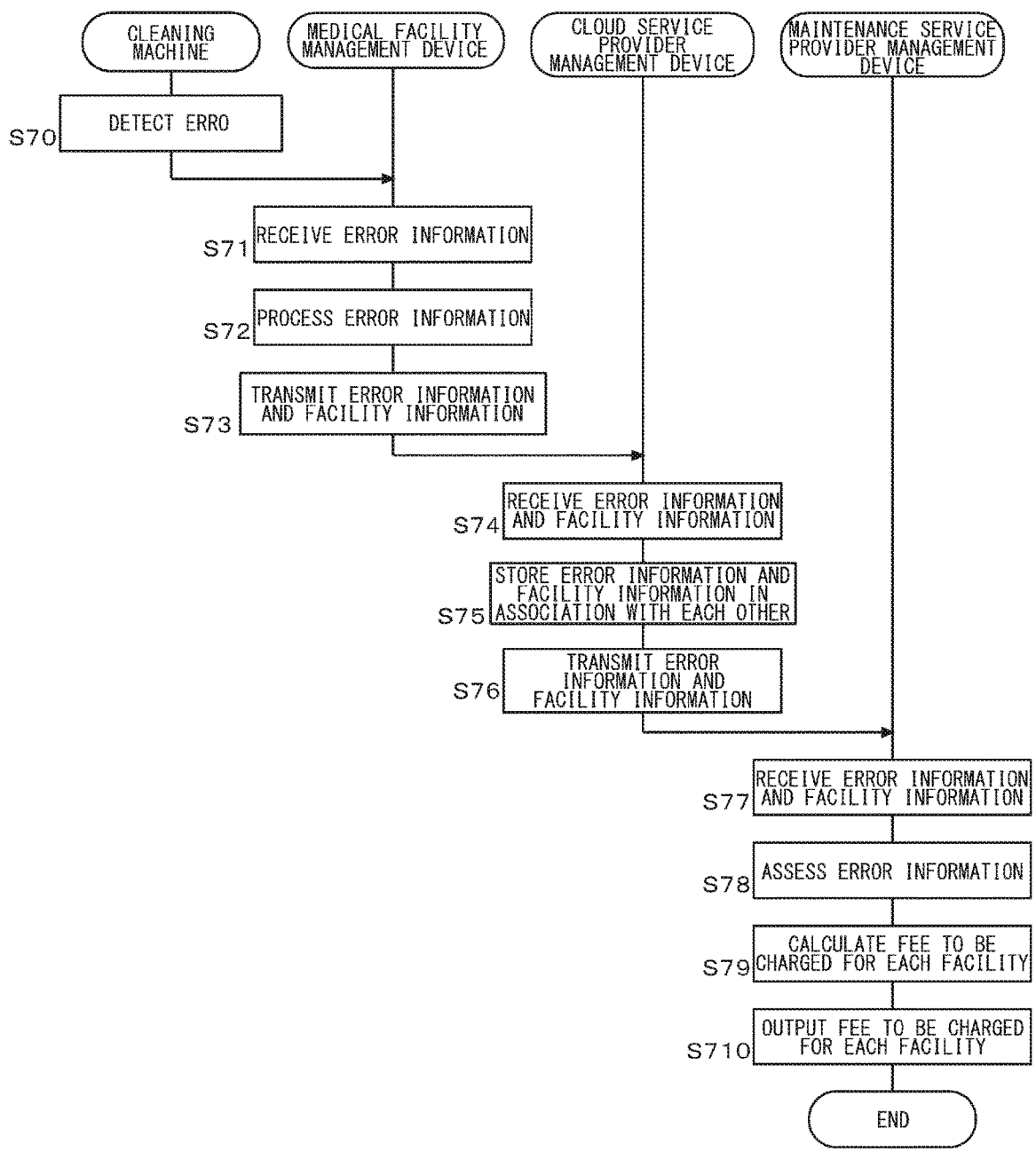
FIG. 20 is a flow chart showing the flow of a fee-setting process according to the first exemplary variation.

FIG. 20 is a flow chart showing the flow of a fee-setting process according to the first exemplary variation. The processing unit 41 of the cleaning machine 40 detects an error related to the use of the cleaning machine 40 (S70). The processing unit 41 passes error information including error detection to the communication unit 43, and the communication unit 43 transmits the error information to the medical facility management device 30 via the internal network. The communication unit 33 of the medical facility management device 30 receives the error information from the cleaning machine 40 and passes the error information to the processing unit 31 (S71). The processing unit 31 processes the received error information (S72). The processing unit 31 adds facility information regarding the medical facility to the processed error information and passes the processed error information to the communication unit 33. The communication unit 33 transmits the error information and the facility information to the cloud service provider management device 20 via the external network 2 (S73).

The communication unit 23 of the cloud service provider management device 20 receives the error information and the facility information via the external network 2 and passes the error information and the facility information to the processing unit 21 (S74). The processing unit 21 stores the error information and the facility information that have been received, in association with each other in the error information table 221 (S75). The processing unit 21 reads the error information and the facility information stored in the error information table 221 and passes the error information and the facility information to the communication unit 23 at a predetermined timing, and the communication unit 23 transmits the error information and the facility information to the maintenance service provider management device 10 via the external network 2 (S76). The predetermined timing may be a timing at which a transmission request is received from the maintenance service provider management device 10 or a timing at which a predetermined date and time has arrived.

The communication unit 13 of the maintenance service provider management device 10 receives the error information and the facility information via the external network 2 and passes the error information and the facility information to the processing unit 11 (S77). The assessment unit 111 assesses the received error information (S78). More specifically, the assessment unit 111 reads the evaluation reference information in the evaluation table 122, compares the error information with the evaluation reference information, and assesses whether or not the cleaning machine 40 has been used appropriately. At this time, the degree of appropriateness regarding the use of the cleaning machine 40 may be ranked based on the degree of deviation between the two.

The calculation unit 112 reads fee information corresponding to various errors relating to the cleaning machine 40 from the fee table 123. The calculation unit 112 calculates a fee to be charged (for example, a maintenance fee) for each facility based on the fee information that has been read, the assessment result by the assessment unit 111, and the facility information (S79). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S710).

Second Exemplary Variation

Figure 21:
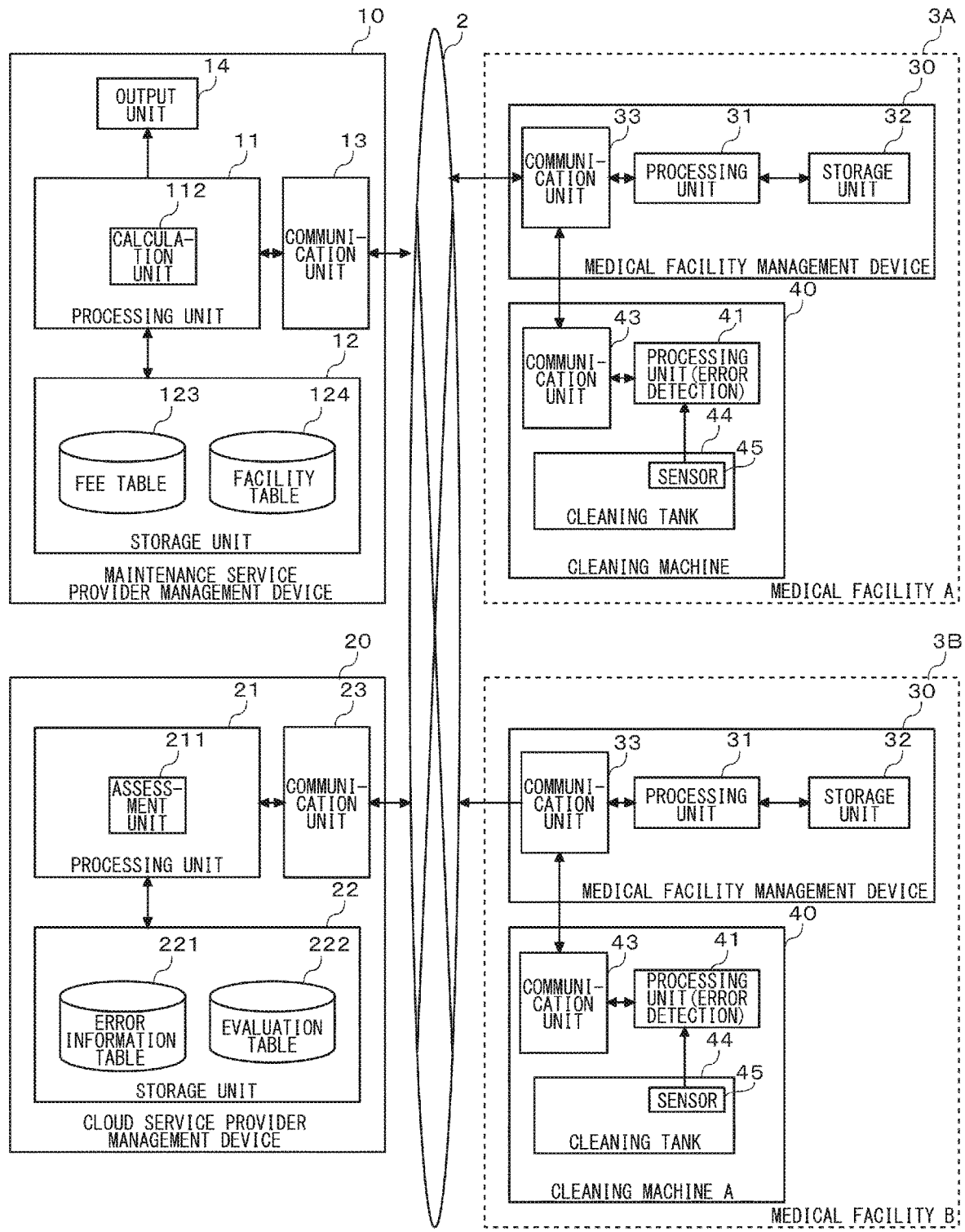
FIG. 21 is a block diagram showing the configuration of a fee-setting system according to the second exemplary variation of the present invention.

FIG. 21 is a block diagram showing the configuration of a fee-setting system 1 according to the second exemplary variation of the present invention. In the second exemplary variation, the processing unit 21 of the cloud service provider management device 20 includes an assessment unit 211, and the storage unit 22 of the cloud service provider management device 20 includes an error information table 221 and an evaluation table 222. The processing unit 11 of the maintenance service provider management device 10 includes a calculation unit 112, and the storage unit 12 of the maintenance service provider management device 10 includes a fee table 123 and a facility table 124.

Figure 22:
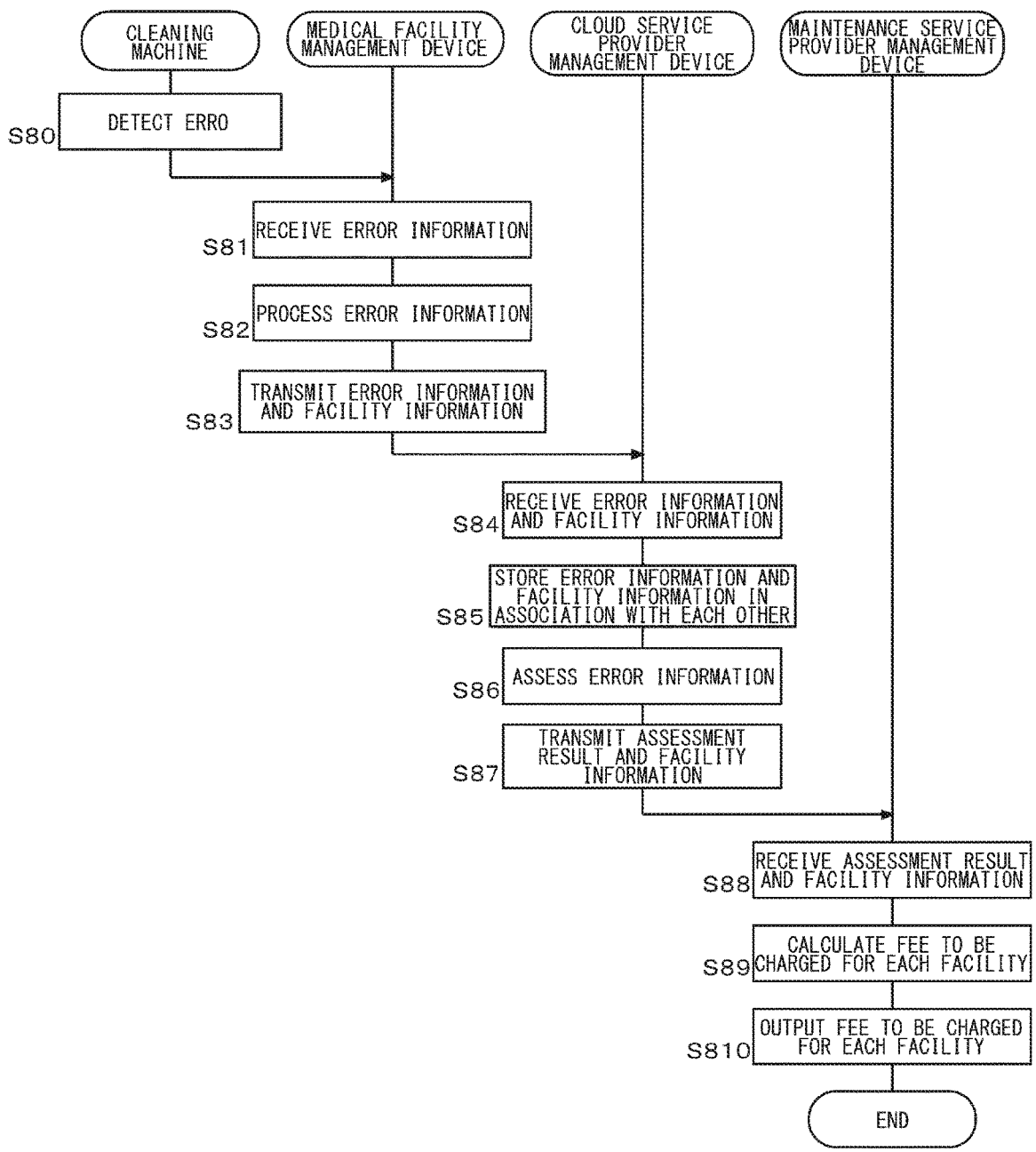
FIG. 22 is a flow chart showing the flow of a fee-setting process according to the second exemplary variation.

FIG. 22 is a flow chart showing the flow of a fee-setting process according to the second exemplary variation. The processing unit 41 of the cleaning machine 40 detects an error related to the use of the cleaning machine 40 (S80). The processing unit 41 passes error information including error detection to the communication unit 43, and the communication unit 43 transmits the error information to the medical facility management device 30 via the internal network. The communication unit 33 of the medical facility management device 30 receives the error information from the cleaning machine 40 and passes the error information to the processing unit 31 (S81). The processing unit 31 processes the received error information (S82). The processing unit 31 adds facility information regarding the medical facility to the processed error information and passes the processed error information to the communication unit 33. The communication unit 33 transmits the error information and the facility information to the cloud service provider management device 20 via the external network 2 (S83).

The communication unit 23 of the cloud service provider management device 20 receives the error information and the facility information via the external network 2 and passes the error information and the facility information to the processing unit 21 (S84). The processing unit 21 stores the error information and the facility information that have been received, in association with each other in the error information table 221 (S85). At a predetermined timing, the assessment unit 211 reads the error information and the facility information stored in the error information table 221 and assesses the error information that has been read (S86). More specifically, the assessment unit 211 reads the evaluation reference information in the evaluation table 222, compares the error information with the evaluation reference information, and assesses whether or not the cleaning machine 40 has been used appropriately. At this time, the degree of appropriateness regarding the use of the cleaning machine 40 may be ranked based on the degree of deviation between the two.

The assessment unit 211 passes the assessment result and the facility information to the communication unit 23, and the communication unit 23 transmits the assessment result and the facility information to the maintenance service provider management device 10 via the external network 2 (S87). The communication unit 13 of the maintenance service provider management device 10 receives the assessment result and the facility information via the external network 2 and passes the assessment result and the facility information to the processing unit 11 (S88).

The calculation unit 112 reads fee information corresponding to various errors relating to the cleaning machine 40 from the fee table 123. The calculation unit 112 calculates a fee to be charged (for example, a maintenance fee) for each facility based on the fee information that has been read and the assessment result and the facility information that have been received (S89). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 211. The calculation unit 112 stores the calculated fee to be charged and the facility information in the facility table 124 in association with each other. Caused by a user's operation, the output unit 14 outputs the fee to be charged and the facility information stored in the facility table 124 (S810).

Third Exemplary Variation

Figure 23:
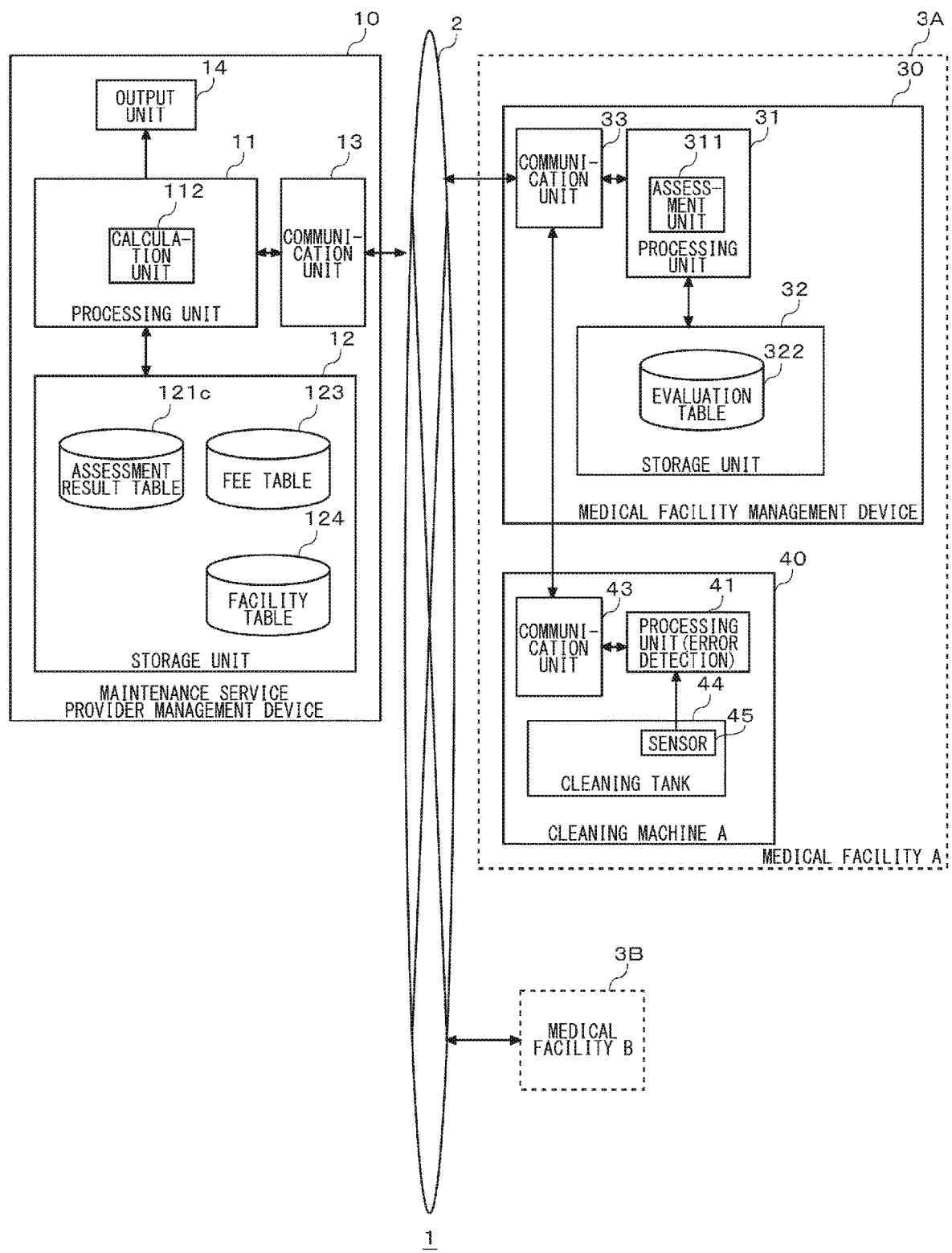
FIG. 23 is a block diagram showing the configuration of a fee-setting system according to the third exemplary variation of the present invention.

FIG. 23 is a block diagram showing the configuration of a fee-setting system 1 according to the third exemplary variation of the present invention. The third exemplary variation is an example in which the process of assessing error information is performed by the medical facility management device 30. In the third exemplary variation, the cloud service provider management device 20 is not used. The processing unit 11 of the maintenance service provider management device 10 includes a calculation unit 112, and the storage unit 12 of the maintenance service provider management device 10 includes an assessment result table 121c, a fee table 123, and a facility table 124. The processing unit 31 of the medical facility management device 30 includes an assessment unit 311, and the storage unit 32 of the medical facility management device 30 includes an evaluation table 322.

Figure 24:
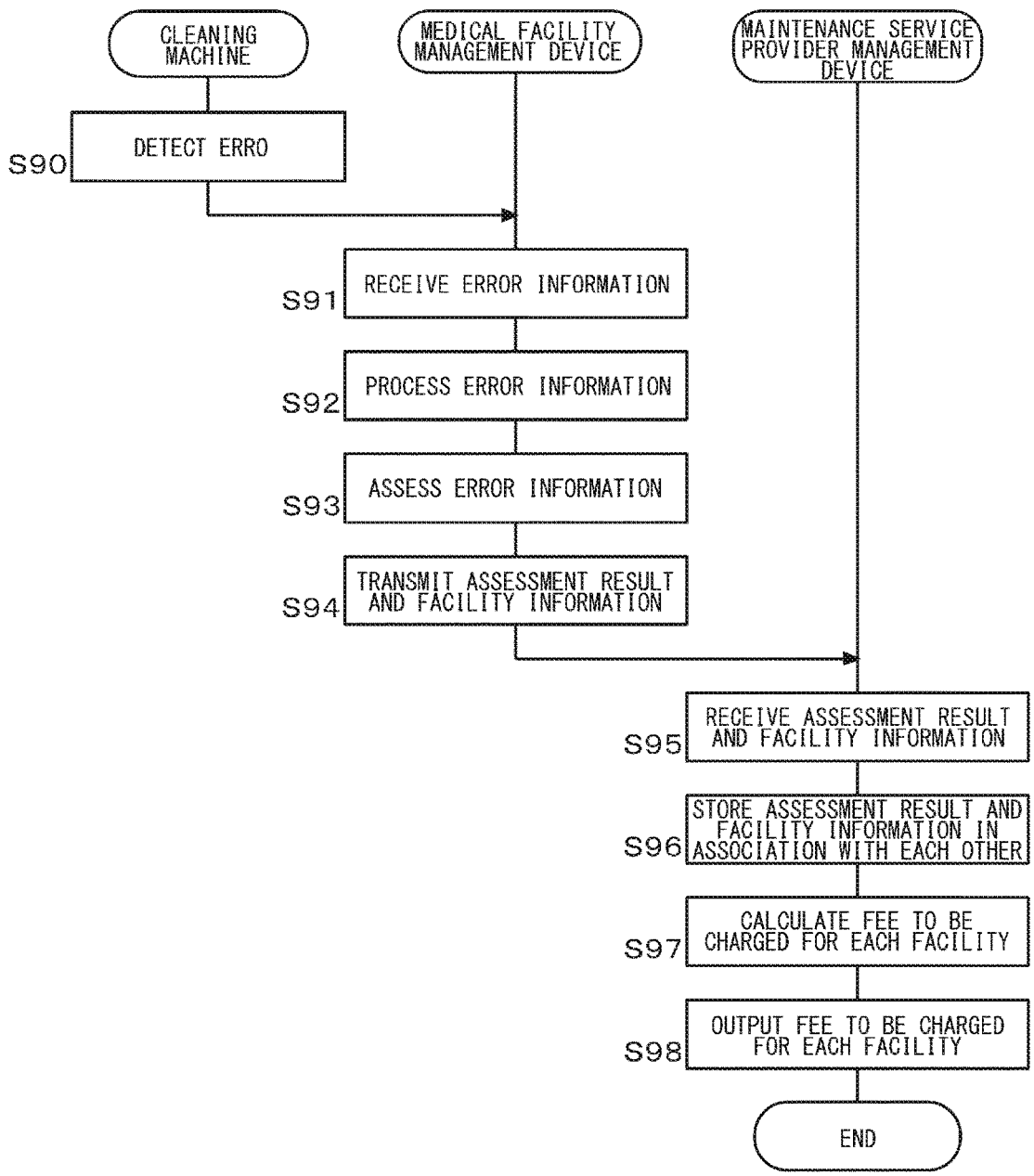
FIG. 24 is a flow chart showing the flow of a fee-setting process according to the third exemplary variation.

FIG. 24 is a flow chart showing the flow of a fee-setting process according to the third exemplary variation. The processing unit 41 of the cleaning machine 40 detects an error related to the use of the cleaning machine 40 (S90). The processing unit 41 passes error information including error detection to the communication unit 43, and the communication unit 43 transmits the error information to the medical facility management device 30 via the internal network. The communication unit 33 of the medical facility management device 30 receives the error information from the cleaning machine 40 and passes the error information to the processing unit 31 (S91). The processing unit 31 processes the received error information (S92). The assessment unit 311 assesses the processed error information (S93). More specifically, the assessment unit 311 reads the evaluation reference information in the evaluation table 322, compares the error information with the evaluation reference information, and assesses whether or not the cleaning machine 40 has been used appropriately. At this time, the degree of appropriateness regarding the use of the cleaning machine 40 may be ranked based on the degree of deviation between the two.

The assessment unit 311 adds the facility information regarding the medical facility to the assessment result and passes the assessment result to the communication unit 33. The communication unit 33 transmits the assessment result and the facility information to the maintenance service provider management device 10 via the external network 2 (S94). The communication unit 13 of the maintenance service provider management device 10 receives the assessment result and the facility information via the external network 2 and passes the assessment result and the facility information to the processing unit 11 (S95). The processing unit 11 stores the assessment result and the facility information that have been received, in association with each other in the assessment result table 121c (S96).

At a predetermined timing, the calculation unit 112 reads fee information corresponding to various errors related to the cleaning machine 40 from the fee table 123 and reads the assessment result and the facility information from the assessment result table 121c. The calculation unit 112 calculates a fee to be charged (for example, a maintenance fee) for each facility based on the fee information that has been read and the assessment result and the facility information that have been read (S97). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 311. The calculation unit 112 stores the calculated fee to be charged and the facility information in the facility table 124 in association with each other. Caused by a user's operation, the output unit 14 outputs the fee to be charged and the facility information stored in the facility table 124 (S98).

Fourth Exemplary Variation

Figure 25:
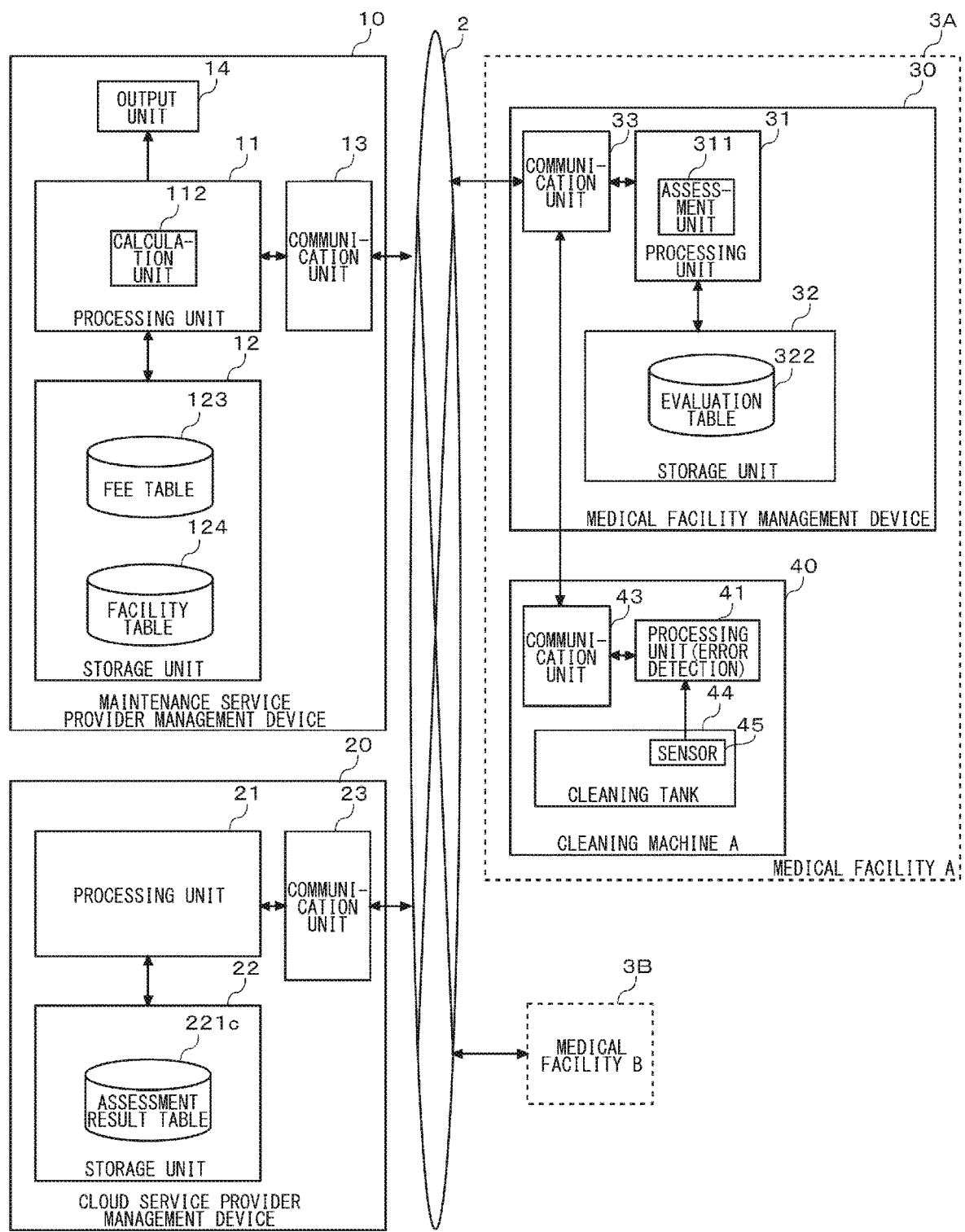
FIG. 25 is a block diagram showing the configuration of a fee-setting system according to the fourth exemplary variation of the present invention.

FIG. 25 is a block diagram showing the configuration of a fee-setting system 1 according to the fourth exemplary variation of the present invention. In the fourth exemplary variation, the cloud service provider management device 20 is also used. In the fourth exemplary variation, the processing unit 11 of the maintenance service provider management device 10 includes a calculation unit 112, and the storage unit 12 of the maintenance service provider management device 10 includes a fee table 123 and a facility table 124. The storage unit 22 of the cloud service provider management device 20 includes an assessment result table 121c. The processing unit 31 of the medical facility management device 30 includes an assessment unit 311, and the storage unit 32 of the medical facility management device 30 includes an evaluation table 322.

Figure 26:
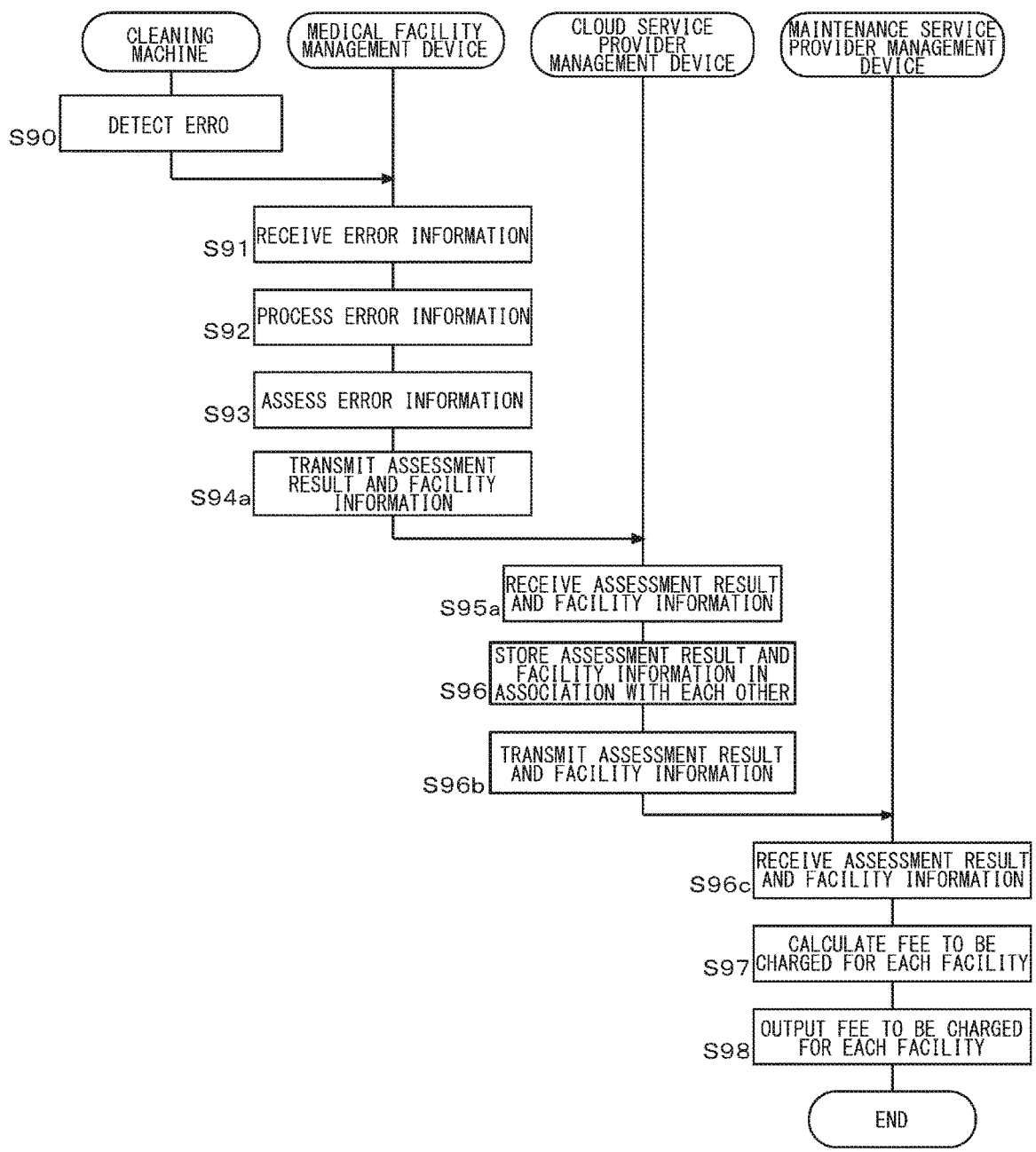
FIG. 26 is a flow chart showing the flow of a fee-setting process according to the fourth exemplary variation.

FIG. 26 is a flow chart showing the flow of a fee-setting process according to the fourth exemplary variation. The processing unit 41 of the cleaning machine 40 detects an error related to the use of the cleaning machine 40 (S90). The processing unit 41 passes error information including error detection to the communication unit 43, and the communication unit 43 transmits the error information to the medical facility management device 30 via the internal network. The communication unit 33 of the medical facility management device 30 receives the error information from the cleaning machine 40 and passes the error information to the processing unit 31 (S91). The processing unit 31 processes the received error information (S92). The assessment unit 311 assesses the processed error information (S93). More specifically, the assessment unit 311 reads the evaluation reference information in the evaluation table 322, compares the error information with the evaluation reference information, and assesses whether or not the cleaning machine 40 has been used appropriately. At this time, the degree of appropriateness regarding the use of the cleaning machine 40 may be ranked based on the degree of deviation between the two.

The assessment unit 311 adds the facility information regarding the medical facility to the assessment result and passes the assessment result to the communication unit 33. The communication unit 33 transmits the assessment result and the facility information to the cloud service provider management device 20 via the external network 2 (S94a). The communication unit 23 of the cloud service provider management device 20 receives the assessment result and the facility information via the external network 2 and passes the assessment result and the facility information to the processing unit 21 (S95a). The processing unit 21 stores the assessment result and the facility information that have been received, in association with each other in the assessment result table 221c (S96a). The processing unit 21 reads the assessment result and the facility information stored in the assessment result table 221c and passes the assessment result and the facility information to the communication unit 23 at a predetermined timing, and the communication unit 23 transmits the assessment result and the facility information to the maintenance service provider management device 10 via the external network 2 (S96b).

The communication unit 13 of the maintenance service provider management device 10 receives the assessment result and the facility information via the external network 2 and passes the assessment result and the facility information to the processing unit 11 (S96c). The calculation unit 112 reads fee information corresponding to various errors relating to the cleaning machine 40 from the fee table 123. The calculation unit 112 calculates a fee to be charged (for example, a maintenance fee) for each facility based on the fee information that has been read and the assessment result and the facility information that have been received (S97). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 311. The calculation unit 112 stores the calculated fee to be charged and the facility information in the facility table 124 in association with each other. Caused by a user's operation, the output unit 14 outputs the fee to be charged and the facility information stored in the facility table 124 (S98).

Fifth Exemplary Variation

Figure 27:
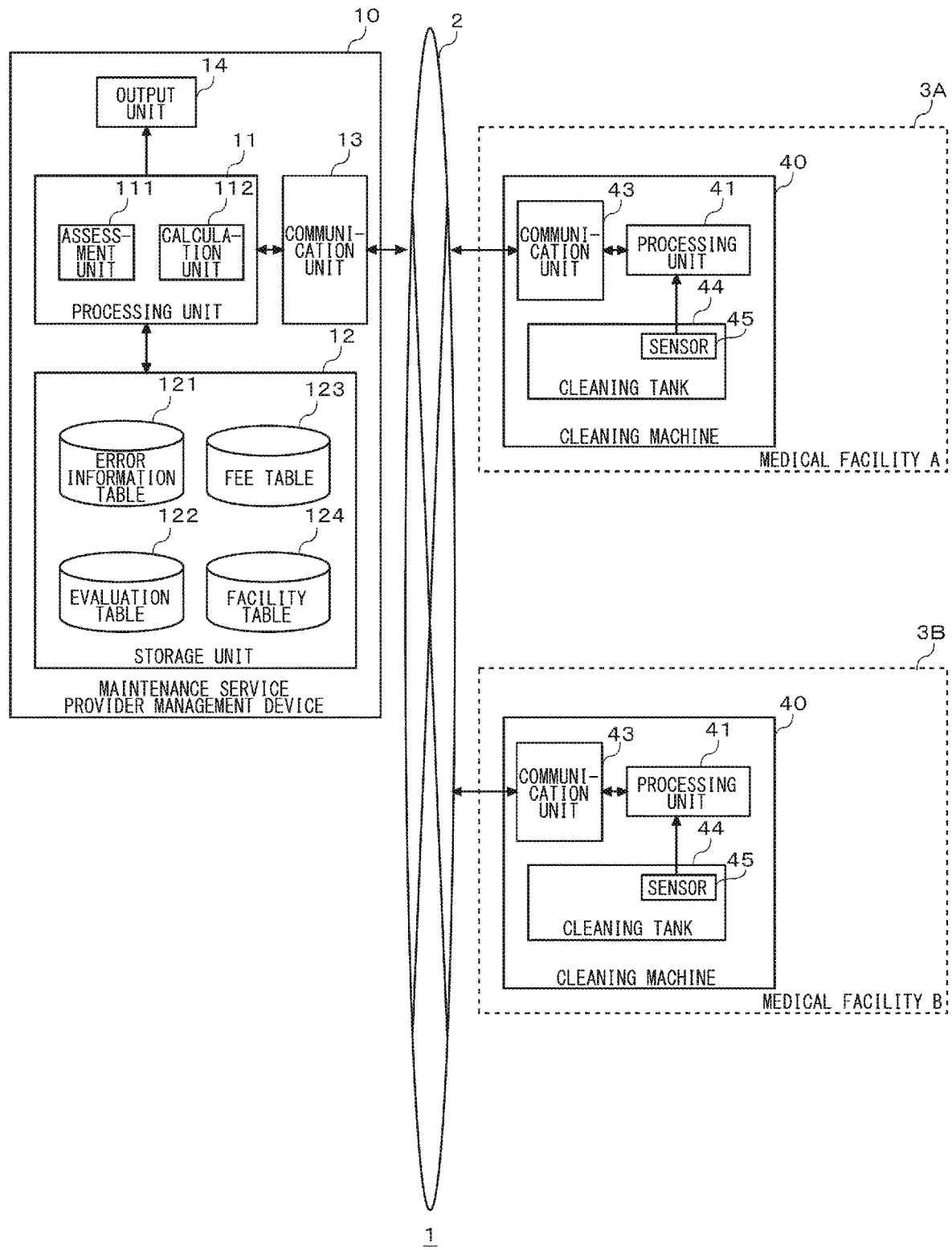
FIG. 27 is a block diagram showing the configuration of a fee-setting system according to the fifth exemplary variation of the present invention.

FIG. 27 is a block diagram showing the configuration of a fee-setting system 1 according to the fifth exemplary variation of the present invention. The fifth exemplary variation represents an example where the cleaning machine 40 directly transmits error information and facility information to the maintenance service provider management device 10 without going through the medical facility management device 30.

Figure 28:
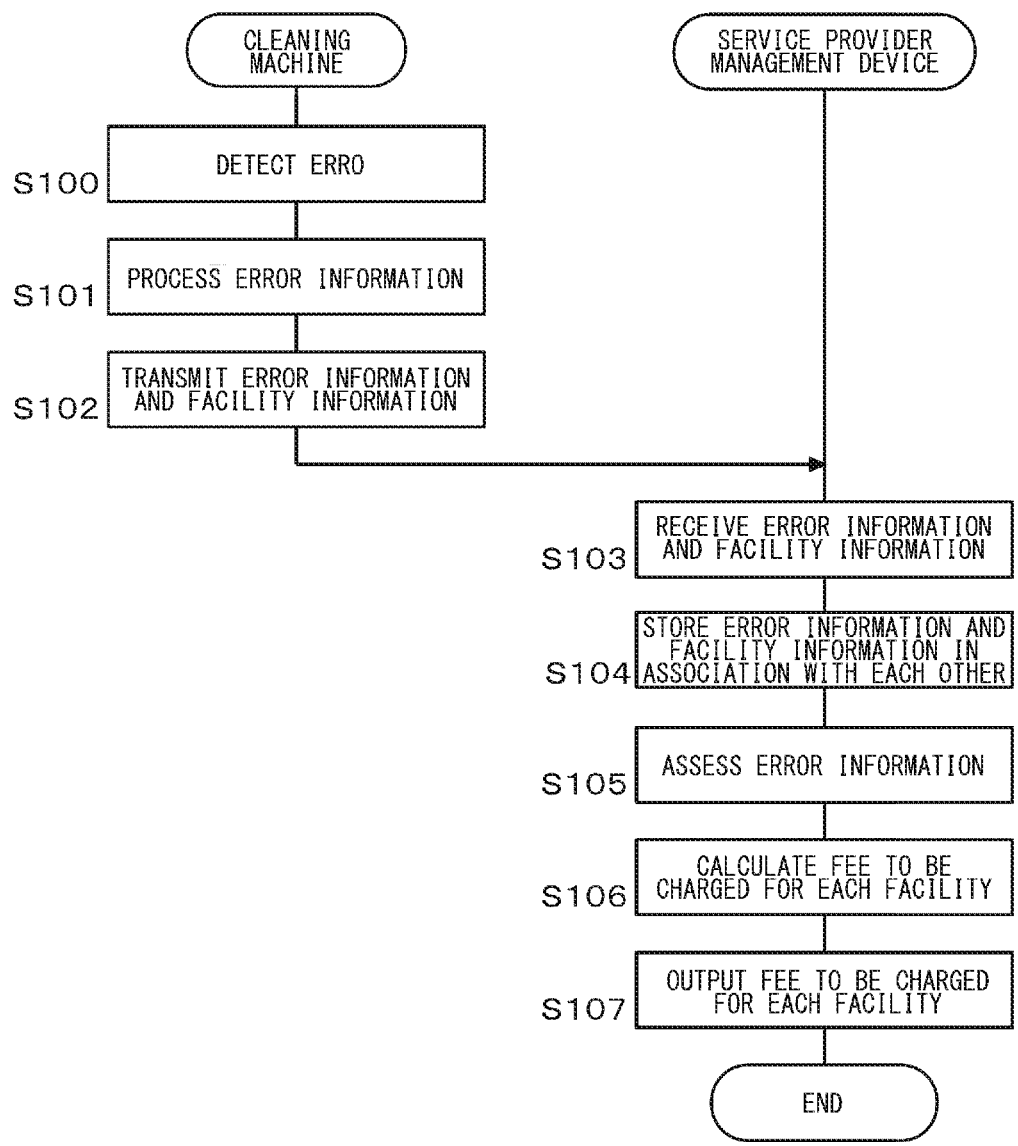
FIG. 28 is a flow chart showing the flow of a fee-setting process according to the fifth exemplary variation.

FIG. 28 is a flow chart showing the flow of a fee-setting process according to the fifth exemplary variation. The processing unit 41 of the cleaning machine 40 detects an error related to the use of the cleaning machine 40 (S100). The processing unit 41 processes the detected error information (S101). The processing unit 41 adds facility information regarding the medical facility to the processed error information and passes the processed error information to the communication unit 43. The communication unit 43 transmits the error information and the facility information to the medical facility management device 30 via the external network 2 (S102).

The communication unit 13 of the maintenance service provider management device 10 receives the error information and the facility information via the external network 2 and passes the error information and the facility information to the processing unit 11 (S103). The processing unit 11 stores the error information and the facility information that have been received in association with each other in the error information table 121 (S104). At a predetermined timing, the assessment unit 111 reads the error information and the facility information stored in the error information table 121 and assesses the error information that has been read (S105). More specifically, the assessment unit 111 reads the evaluation reference information in the evaluation table 122, compares the error information with the evaluation reference information, and assesses whether or not the cleaning machine 40 has been used appropriately. At this time, the degree of appropriateness regarding the use of the cleaning machine 40 may be ranked based on the degree of deviation between the two.

The calculation unit 112 reads fee information corresponding to various errors relating to the cleaning machine 40 from the fee table 123. The calculation unit 112 calculates a fee to be charged (for example, a maintenance fee) for each facility based on the fee information that has been read, the assessment result by the assessment unit 111, and the facility information (S106). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S107).

Sixth Exemplary Variation

Figure 29:
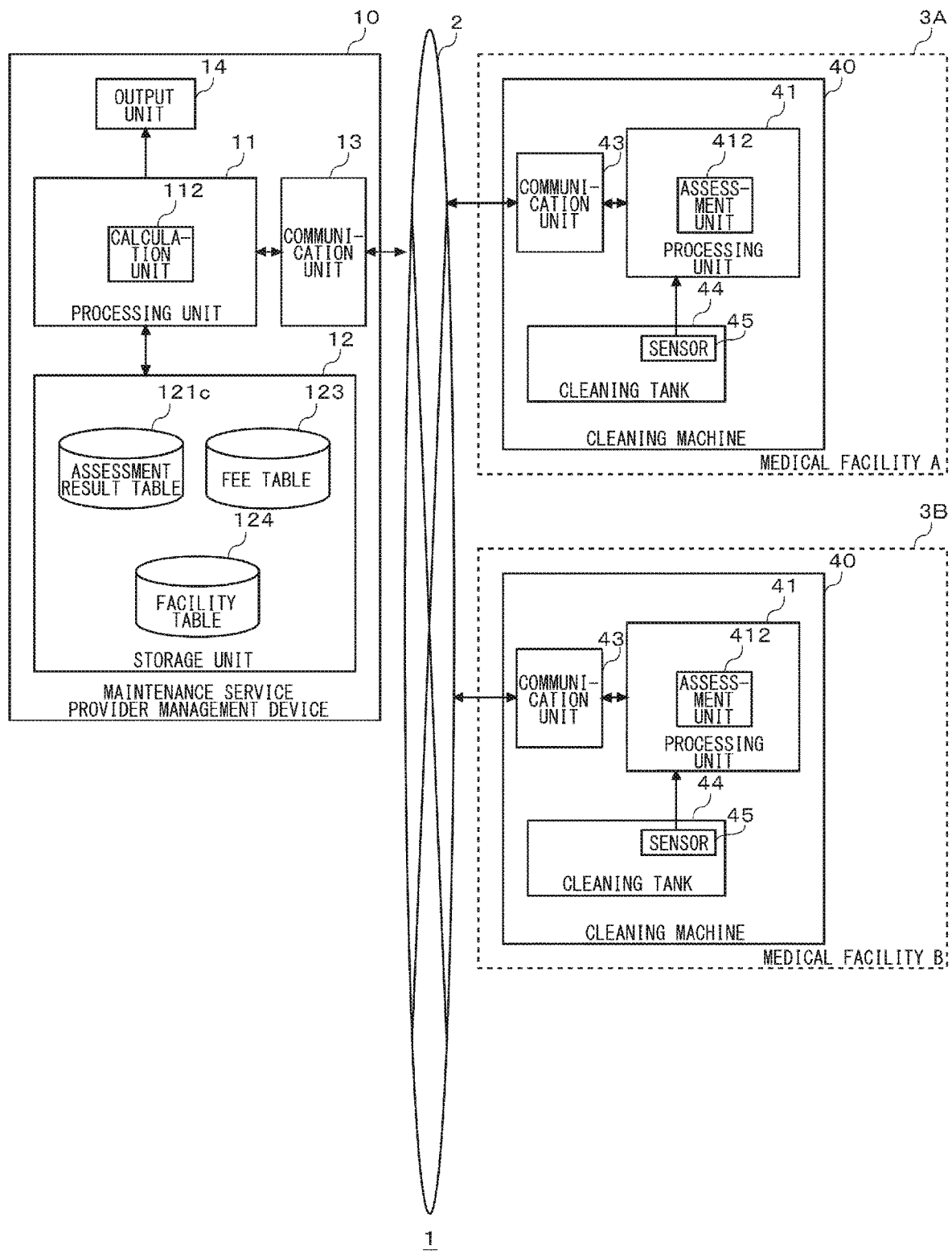
FIG. 29 is a block diagram showing the configuration of a fee-setting system according to the sixth exemplary variation of the present invention.

FIG. 29 is a block diagram showing the configuration of a fee-setting system 1 according to the sixth exemplary variation of the present invention. The sixth exemplary variation represents an example in which the process of assessing error information is also performed by the cleaning machine 40. In this example, an evaluation standard for error information is written in advance in the firmware of the processing unit 41 of the cleaning machine 40.

Figure 30:
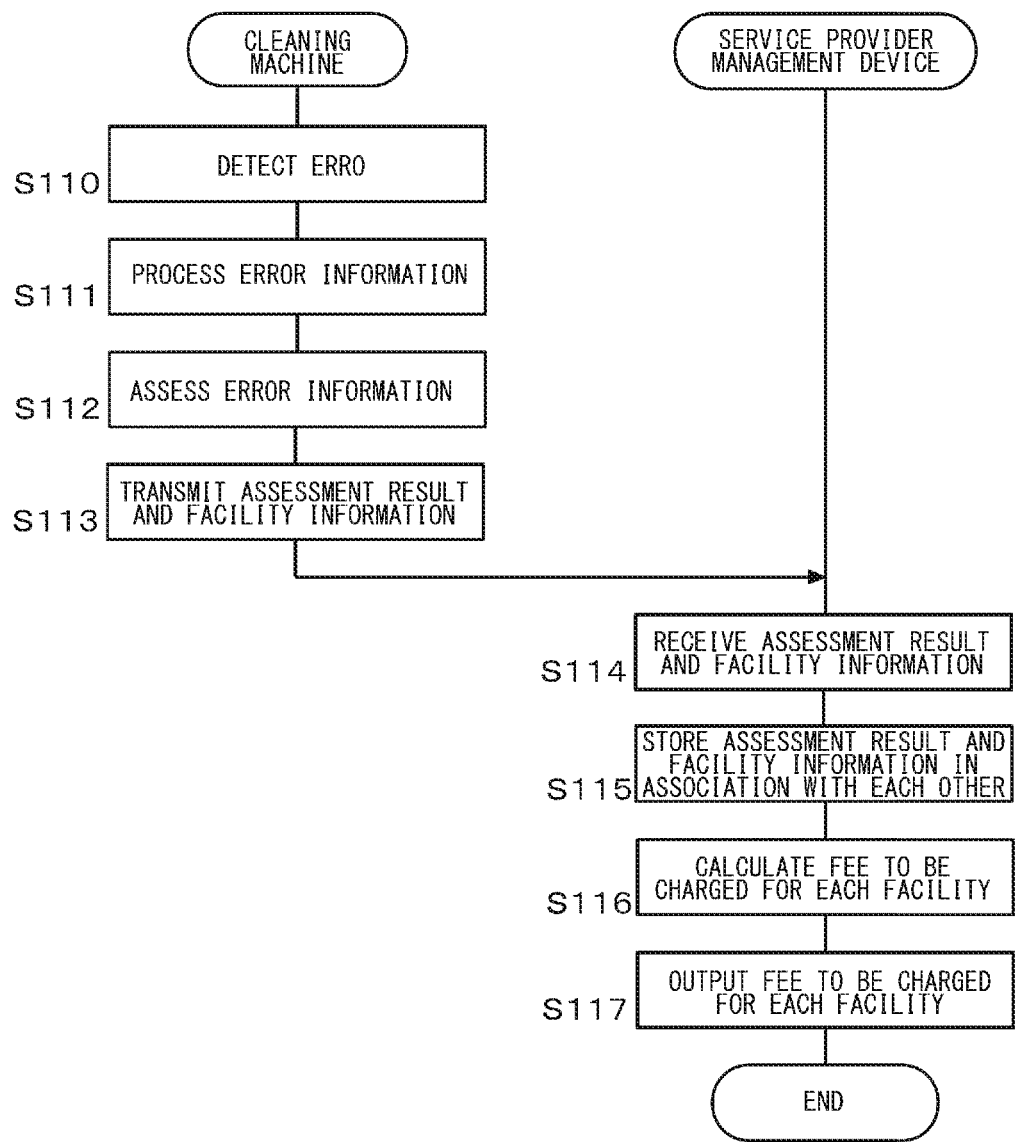
FIG. 30 is a flow chart showing the flow of a fee-setting process according to the sixth exemplary variation.

FIG. 30 is a flow chart showing the flow of a fee-setting process according to the sixth exemplary variation. The processing unit 41 of the cleaning machine 40 detects an error related to the use of the cleaning machine 40 (S110). The processing unit 41 processes the detected error information (S111). The assessment unit 42 assesses the processed error information (S112). More specifically, based on the evaluation standard information that has been set in advance, the assessment unit 42 compares the error information with the evaluation reference information, and assesses whether or not the cleaning machine 40 has been used appropriately. At this time, the degree of appropriateness regarding the use of the cleaning machine 40 may be ranked based on the degree of deviation between the two. The assessment unit 411 adds the facility information regarding the medical facility to the assessment result and passes the assessment result to the communication unit 43. The communication unit 43 transmits the assessment result and the facility information to the medical facility management device 30 via the external network 2 (S113).

The communication unit 13 of the maintenance service provider management device 10 receives the assessment result via the external network 2 and passes the assessment result to the processing unit 11 (S114). The processing unit 11 stores the assessment result and the facility information that have been received, in association with each other in the assessment result table 121c (S115). At a predetermined timing, the calculation unit 112 reads fee information corresponding to various errors related to the cleaning machine 40 from the fee table 123 and reads the assessment result from the assessment result table 121c. The calculation unit 112 calculates a fee to be charged (for example, a maintenance fee) for each facility based on the fee information that has been read, the assessment result by the assessment unit 111, and the facility information (S116). The calculation unit 112 discounts, from the basic fee, the fee corresponding to the ratio of occasions where the cleaning machine 40 was appropriately used, and calculate a final fee to be charged. At this time, the fee to be charged for each facility may be calculated in comparison with the degree of appropriateness regarding the use of the cleaning machine 40 ranked by the assessment unit 111. The calculation unit 112 stores the calculated fee to be charged and the facility information in the facility table 124 in association with each other. Caused by a user's operation, the output unit 14 outputs the fee to be charged and the facility information stored in the facility table 124 (S117).

In the first, second, and fourth exemplary variations described above, examples have been described in which part of the functions of the maintenance service provider management device 10 are outsourced to a cloud service provider. In this regard, all the functions of the maintenance service provider management device 10 may be outsourced to the cloud service provider. In this case, the "maintenance service provider management device 10" in the first to sixth embodiments and the third, fifth, and sixth exemplary variations may be replaced with the "cloud service provider management device 20". In the fifth and sixth exemplary variations, part of the functions of the maintenance service provider management device 10 may be executed by the cloud service provider management device 20.

In the above-described second and third embodiments, examples of assessing the usage status of the consumable items of the cleaning machine 40 have been described. In this regard, the consumable items of the endoscopic system 50 include, for example, a lamp of the light source device 54. Model number information from a tag such as an RFID attached to a regular lamp is read using a reader (not shown) installed in the light source device 54 so as to thereby detect whether or not the lamp is a regular product and the installation date. The consumables items of a scope include, for example, accessories that can be attached to and detached from the scope such as air/water feeding buttons, suction buttons, forceps plugs, and distal end hoods. Model number information from a tag such as an RFID attached to a regular accessory is read using a reader (not shown) installed in any one of the light source device 54, the endoscope processing device 51, the scope 55, and the cleaning machine 40 so as to thereby detect whether or not the accessory is a regular product and the installation date.

In the same way, consumables items for a treatment device (not shown) that cuts or seals blood vessels, mucous membranes, and the like using thermal energy or ultrasonic energy include, for example, treatment parts that are worn, deformed, or destroyed by heat. The treatment device monitors the status of the treatment parts and records error information when an abnormality is detected. Thus, it is possible to assess whether or not a treatment part has been replaced at an appropriate time by comparing the date when the abnormality of the treatment part was detected with the replacement date of the treatment part.

In the above description, as an example of assessing the degree of appropriateness regarding the use of a medical device, an example of assessing the degree of appropriateness regarding the use of the cleaning machine 40, the scope 55, the endoscopic system 50, the water leakage detector 60, and the storage 70 has been described. In this regard, the medical device is not limited to these devices used in the endoscopy department and includes devices used in other departments such as the radiation department.

What is claimed is:

1. A fee-setting system comprising:
   a storage unit that stores a fee table that is set in accordance with how a cleaning device for an endoscope is used; and
   a processor comprising hardware, wherein the processor is configured to:
      assess the degree of appropriateness in a medical facility regarding the use of the cleaning device relating to medical treatment used in the medical facility based on the degree of deviation and information regarding the medical facility, in which the degree of deviation that is obtained by comparing information indicating the usage status of the cleaning device that has been detected by a sensor for detecting the usage status of the cleaning device with reference information regarding the method of using the cleaning device;
      calculate a fee to be charged to the medical facility based on the degree of appropriateness;
      acquire error information related to a user's incorrect operation on the device detected as the usage status by the sensor; and
      assess whether or not the device has been appropriately used by comparing the error information with reference information regarding the operation method of the device:
      acquire the detection value of at least one of (i) the flow rate and (ii) the pressure of a liquid for the cleaning device to clean the endoscope that has been detected as the usage status by the sensor;
      assess whether or not the endoscope has been appropriately set in the cleaning device by performing at least one of (i) a comparison between the detection value of the flow rate and a reference value of the flow rate of the liquid and (ii) a comparison between the detection value of the pressure and a reference value of the pressure of the liquid; and
      calculate the fee to be charged to the medical facility based on the degree of appropriateness and the fee table.

2. The fee-setting system according to claim 1, wherein the processor is configured to rank the degree of appropriateness regarding the use of the device based on the degree of deviation.

3. The fee-setting system according to claim 1, wherein the processor is configured to:
   acquire at least one of (i) the latest and previous maintenance dates of the cleaning device and (ii) the use count of the cleaning device that have been detected as the usage status by the sensor; and
   assess whether or not maintenance has been performed on the cleaning device at an appropriate time by performing at least one of (i) a comparison between the acquired value of a maintenance period calculated from the latest maintenance date and the previous maintenance date and a reference value of a maintenance period of the cleaning device and (ii) a comparison between the acquired value of the use count of the cleaning device and a reference value of the use count of the cleaning device.

4. The fee-setting system according to claim 1, wherein the processor is configured to acquire at least one of (i) the replacement date, (ii) use count, and (iii) number of days of use of a consumable item of the cleaning device that have been detected as the usage status by the sensor; and
   assess whether or not the consumable item has been replaced at an appropriate time by performing at least one of (i) a comparison between the replacement date of the consumable item and the expiration date of the consumable item, (ii) a comparison between the acquired value of the use count of the consumable item and a reference value of the use count of the consumable item, and (iii) a comparison between the acquired value of the number of days of use of the consumable item and a reference value of the number of days of use of the consumable item.

5. The fee-setting system according to claim 1, wherein the processor is configured to:
acquire the model number of the consumable item of the cleaning device detected as the usage status by the sensor; and
assess whether or not the consumable item has been replaced with an appropriate product by comparing the model number of the consumable item that has been detected with the model number of the regular product of the consumable item.

6. The fee-setting system according to claim 1, wherein the processor is configured to:
acquire the number of days from when the endoscope was used to when the endoscope was inspected for water leakage that has been detected as the usage status by the sensor; and
assess whether or not the endoscope has been inspected for water leakage at an appropriate time by comparing the acquired value of the number of days from when the endoscope was used to when the endoscope was inspected for water leakage with a reference value of the number of days from when the endoscope is used to when the endoscope is inspected for water leakage.

7. The fee-setting system according to claim 1, wherein the processor is configured to:
acquire
(i) a detection date on which water leakage of the endoscope was detected,
(ii) a maintenance date on which maintenance was performed on the endoscope, and
(iii) an examination date of an examination
in which the endoscope was used that have been detected as the usage status by the sensor; and
assess whether or not the endoscope has been used appropriately by comparing the chronological order of the detection date, the maintenance date, and the examination date with usage standard information of the endoscope at the time when the water leakage was detected.

8. The fee-setting system according to claim 1, wherein the processor is configured to:
acquire the number of days from when the endoscope was used to when the endoscope was cleaned that has been detected as the usage status by the sensor; and
assess whether or not the endoscope has been cleaned at an appropriate time by comparing the acquired value of the number of days from when the endoscope was used to when the endoscope was cleaned with a reference value of the number of days from when the endoscope is used to when the endoscope is cleaned.

9. The fee-setting system according to claim 1, wherein the processor is configured to:
acquire the number of days from when the endoscope was cleaned to when the endoscope started being stored in a storage that has been detected as the usage status by the sensor; and
assess whether or not the endoscope has been stored in the storage at an appropriate time by comparing the acquired value of the number of days from when the endoscope was cleaned to when the endoscope started being stored in the storage with a reference value of the number of days from when the endoscope is cleaned to when the endoscope starts being stored in the storage.

10. The fee-setting system according to claim 1, wherein the processor is configured to:
acquire the number of days from when the endoscope started being stored in the storage to when the endoscope was used that has been detected as the usage status by the sensor; and
assess whether or not the endoscope has been used at an appropriate time by comparing the acquired value of the number of days from when the endoscope started being stored in the storage to when the endoscope was used with a reference value of the number of days from when the endoscope starts being stored in the storage to when the endoscope is used.

11. The fee-setting system according to claim 1, wherein the processor is configured to calculate the fee to be charged to the medical facility based on the degree of appropriateness and at least one of the number of qualified persons who belong to the medical facility and the qualification level of the qualified persons.

12. The fee-setting system according to claim 1, wherein the processor is configured to:
rank the degree of appropriateness regarding the use of the cleaning device based on the degree of deviation obtained by comparing information indicating the usage status of the cleaning device with reference information regarding the method of using the cleaning device; and
calculate the fee to be charged to the medical facility based on at least one of (i) the rank, (ii) the type of information indicating the usage status, and (iii) the frequency at which the cleaning device has not been used appropriately.

13. A fee-setting system comprising:
a storage unit that stores a fee table that is set in accordance with how a cleaning device for an endoscope is used; and
a processor comprising hardware, wherein the processor is configured to:
assess the degree of appropriateness in a medical facility regarding the use of the cleaning device relating to medical treatment used in the medical facility based on the degree of deviation and information regarding the medical facility, in which the degree of deviation that is obtained by comparing information indicating the usage status of the cleaning device that has been detected by a sensor for detecting the usage status of the cleaning device with reference information regarding the method of using the cleaning device;
output a fee to be charged to the medical facility that has been calculated based on the degree of appropriateness and the information regarding the medical facility
acquire error information related to a user's incorrect operation on the device detected as the usage status by the sensor; and
assess whether or not the device has been appropriately used by comparing the error information with reference information regarding the operation method of the device:
acquire the detection value of at least one of (i) the flow rate and (ii) the pressure of a liquid for the cleaning device to clean the endoscope that has been detected as the usage status by the sensor;

assess whether or not the endoscope has been appropriately set in the cleaning device by performing at least one of (i) a comparison between the detection value of the flow rate and a reference value of the flow rate of the liquid and (ii) a comparison between the detection value of the pressure and a reference value of the pressure of the liquid; and calculate the fee to be charged to the medical facility based on the degree of appropriateness and the fee table.

14. A fee-setting method comprising:

storing a fee table that is set in accordance with how a cleaning device for an endoscope is used;

assessing the degree of appropriateness in a medical facility regarding the use of the cleaning device relating to medical treatment used in the medical facility based on the degree of deviation and information regarding the medical facility, in which the degree of deviation that is obtained by comparing information indicating the usage status of the cleaning device that has been detected by a sensor for detecting the usage status of the cleaning device with reference information regarding the method of using the cleaning device;

calculating a fee to be charged to the medical facility based on the degree of appropriateness;

acquiring error information related to a user's incorrect operation on the device detected as the usage status by the sensor; and assessing whether or not the device has been appropriately used by comparing the error information with reference information regarding the operation method of the device:

acquiring the detection value of at least one of (i) the flow rate and (ii) the pressure of a liquid for the cleaning device to clean the endoscope that has been detected as the usage status by the sensor;

assessing whether or not the endoscope has been appropriately set in the cleaning device by performing at least one of (i) a comparison between the detection value of the flow rate and a reference value of the flow rate of the liquid and (ii) a comparison between the detection value of the pressure and a reference value of the pressure of the liquid; and calculating the fee to be charged to the medical facility based on the degree of appropriateness and the fee table.

\* \* \* \* \*